(12) United States Patent
Toure et al.

(10) Patent No.: US 12,168,650 B2
(45) Date of Patent: Dec. 17, 2024

(54) CRYSTALLINE FORMS OF 3-(5-(2-HYDROXY-2-METHYLPROPOXY)-6-METHYLPYRAZIN-2-YL)-1H-INDOLE-7-CARBONITRILE

(71) Applicant: NIDO BIOSCIENCES, INC., Cambridge, MA (US)

(72) Inventors: Bakary-Barry Toure, Weston, MA (US); Magnus Ronn, Melrose, MA (US)

(73) Assignee: NIDO BIOSCIENCES, INC., Cambridge, MA (US)

(*) Notice: Subject to any disclaimer, the term of this patent is extended or adjusted under 35 U.S.C. 154(b) by 55 days.

(21) Appl. No.: 18/154,205

(22) Filed: Jan. 13, 2023

(65) Prior Publication Data

US 2023/0257361 A1    Aug. 17, 2023

Related U.S. Application Data

(60) Provisional application No. 63/299,678, filed on Jan. 14, 2022.

(51) Int. Cl.
*C07D 401/04* (2006.01)
*A61P 35/00* (2006.01)

(52) U.S. Cl.
CPC ............ *C07D 401/04* (2013.01); *A61P 35/00* (2018.01); *C07B 2200/13* (2013.01)

(58) Field of Classification Search
CPC ..... C07D 401/04; C07D 403/04; A61P 35/00; A61P 21/00; C07B 2200/13
See application file for complete search history.

(56) References Cited

U.S. PATENT DOCUMENTS 11,667,624 B2 * 6/2023 Toure ................... C07D 403/04
                                                              514/255.05

FOREIGN PATENT DOCUMENTS

| WO | WO 2015/154169 A1 | 10/2015 |
| WO | WO 2019/222556 A1 | 11/2019 |
| WO | WO 2022/020342 A1 | 1/2022 |

OTHER PUBLICATIONS

U.S. Appl. No. 17/380,736, 2023-0049406, filed Jul. 20, 2021 Feb. 16, 2023, Bakary-Barry Toure.
U.S. Appl. No. 18/172,690, filed Feb. 22, 2023, Bakary-Barry Toure.
U.S. Appl. No. 18/154,205, filed Jan. 13, 2023, Bakary-Barry Toure.
International Search Report and Written Opinion for International Application No. PCT/US2023/060619, mailed Apr. 13, 2023, 16 pages.
Jiang et al., "Synthesis and cytotoxicity evaluation of novel indolylpyrimidines and indolylpyrazines as potential antitumor agents", *Bioorganic & Medicinal Chemistry* 9(5):1149-1154 (2001).

\* cited by examiner

*Primary Examiner* — Jeffrey H Murray
*Assistant Examiner* — Luisalberto Gonzalez
(74) *Attorney, Agent, or Firm* — Lathrop GPM LLP; Brian C. Trinque; Nicole Sassu

(57) ABSTRACT

This disclosure provides crystalline forms of an androgen receptor modulator, and methods of making and using these forms.

13 Claims, 10 Drawing Sheets

CRYSTALLINE FORMS OF 3-(5-(2-HYDROXY-2-METHYLPROPOXY)-6-METHYLPYRAZIN-2-YL)-1H-INDOLE-7-CARBONITRILE

RELATED APPLICATIONS

This application claims priority to U.S. Provisional Application No. 63/299,678 filed on Jan. 14, 2022, the entire content of which is incorporated by reference in its entirety.

BACKGROUND

Prostate cancer is the second leading cause of male cancer-related death in Western countries (Damber, J. E. and Aus, G. Lancet (2008) 371:1710-1721). Numerous studies have shown that the androgen receptor (AR) is central not only to the development of prostate cancer, but also the progression of the disease to the castration resistance state (Taplin, M. E. et al. J. Clin. Oncol. (2003) 21:2673-8; and Tilley, W. D. et al. Cancer Res. (1994) 54:4096-4102). Thus, effective inhibition of human AR remains one of the most effective therapeutic approaches to the treatment of advanced, metastatic prostate cancer.

Spinal and Bulbar Muscular Atrophy (SBMA) or Kennedy's disease, is an x-linked recessively inherited neuromuscular disorder. The main symptoms are weakness and atrophy of bulbar and extremity muscles due to lower motor degeneration in the brainstem and spinal cord together with primary muscle involvement. At onset, patients often manifest limb weakness, cramps, tremor, and contraction fasciculations, especially noticeable in face and tongue. Dysarthria is also common with hypernasality, laryngospasm, and swallowing dysfunctions which frequently result in aspiration pneumonia as the disease progresses. More than half of patients die from respiratory infections diseases. The disease is caused by CAG expansions in exon 1 of the androgen receptor (AR), and androgen is required for the onset. At present there is no treatment for Kennedy's disease.

SUMMARY

Provided herein are crystalline forms useful for the treatment of diseases such as Kennedy's disease in a subject in need thereof. In a particular aspect, provided herein are crystalline forms of 3-(5-(2-hydroxy-2-methylpropoxy)-6-methylpyrazin-2-yl)-1H-indole-7-carbonitrile free base having the formula:

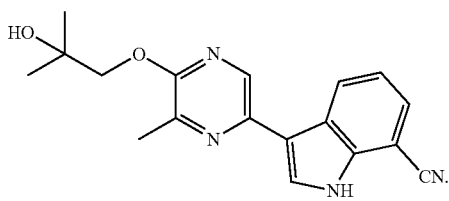 [SMILES: Cc1nc(-c2c[nH]c3c(C#N)cccc23)cnc1OCC(C)(C)O]

In another aspect, provided herein is a method of treating Kennedy's disease in a subject in need thereof comprising administering to the subject a crystalline form of 3-(5-(2-hydroxy-2-methylpropoxy)-6-methylpyrazin-2-yl)-1H-indole-7-carbonitrile free base.

DETAILED DESCRIPTION

Figure 1:
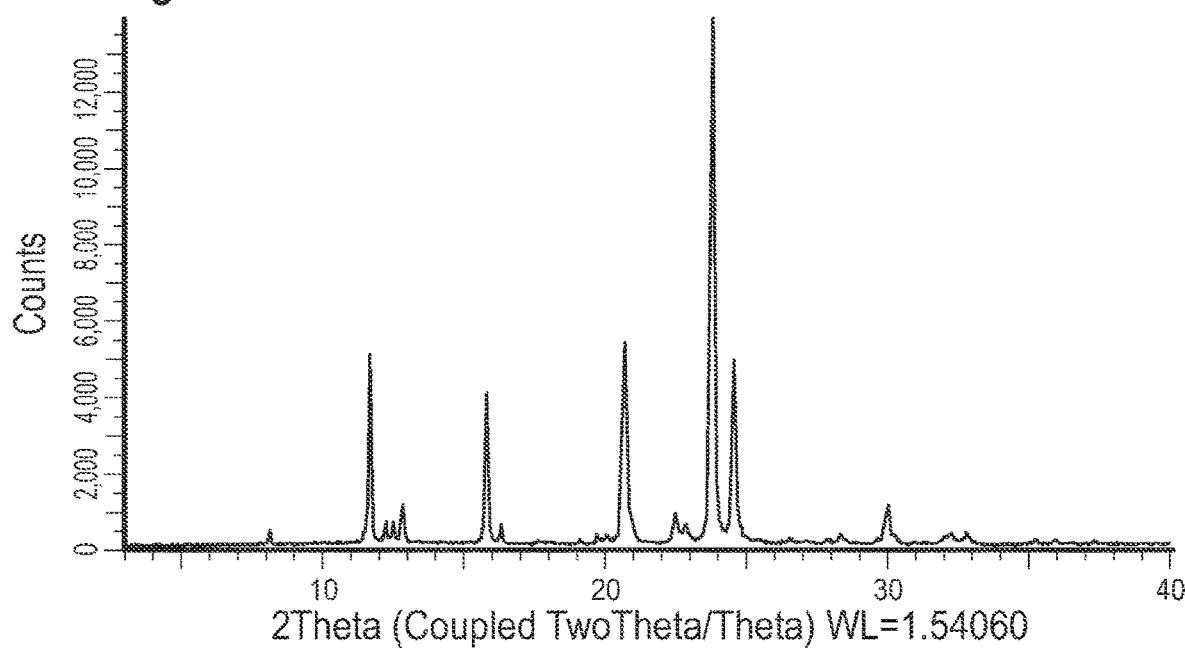
FIG. 1 shows the XRPD diffractogram of crystalline 3-(5-(2-hydroxy-2-methylpropoxy)-6-methylpyrazin-2-yl)-1H-indole-7-carbonitrile anhydrate Form C.

The solid state of a compound can be important when the compound is used for pharmaceutical purposes. The physical properties of a compound can change from one solid form to another, which can affect the suitability of the form for pharmaceutical use. For example, a particular crystalline solid compound can overcome the disadvantage of other solid forms of the compound such as, e.g., instability and/or reduced purity.

Provided herein are solid, crystalline forms of 3-(5-(2-hydroxy-2-methylpropoxy)-6-methylpyrazin-2-yl)-1H-indole-7-carbonitrile:

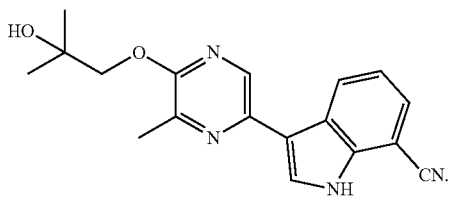 [SMILES: Cc1nc(-c2c[nH]c3c(C#N)cccc23)cnc1OCC(C)(C)O]

This compound is useful for the treatment of a variety of indications, including Kennedy's disease, in a subject.

In particular, provided herein are crystalline forms of 3-(5-(2-hydroxy-2-methylpropoxy)-6-methylpyrazin-2-yl)-1H-indole-7-carbonitrile or a solvate or hydrate thereof.

The compound 3-(5-(2-hydroxy-2-methylpropoxy)-6-methylpyrazin-2-yl)-1H-indole-7-carbonitrile is disclosed in PCT Application No. PCT/US2021/042355 and U.S. patent application Ser. No. 17/380,736, the entire contents of which are incorporated herein by reference.

The crystalline forms provided herein can be characterized by X-ray powder diffraction (XRPD), differential scanning calorimetry (DSC), and thermogravimetric analysis (TGA).

Definitions

Listed below are definitions of various terms used to describe the crystalline forms provided herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which the compound and its crystalline forms belong. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used to herein, the term "$EC_{50}$" refers to the concentration of a compound required to achieve an effect that is 50% of the maximal observed effect of a compound.

As used herein, the term "pharmaceutically acceptable carrier" refers to a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the present disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound provided herein, and not injurious to the patient.

Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound provided herein and are physiologically acceptable to the patient. Supplementary active compounds may also be incorporated into the compositions. Other additional ingredients that may be included in the pharmaceutical compositions used in the practice of the present disclosure are known in the art and described, for example in Remington's Pharmaceutical Sciences (Genaro, Ed., Mack Publishing Co., 1985, Easton, PA), which is incorporated herein by reference.

As used herein, the phrases "therapeutically effective dose" and "therapeutically effective amount" refer to an amount of a compound that prevents the onset, alleviates the symptoms, stops the progression of a disease, or results in another desired biological outcome such as, e.g., improved clinical signs.

The term "treat," "treated," "treating," or "treatment" includes the diminishment or alleviation of at least one symptom associated or caused by the state, disorder or disease being treated. In certain embodiments, the treatment comprises bringing into contact with the opioid receptor an effective amount of the compound provided herein for conditions related to androgen receptors.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. In an embodiment, the patient, subject, or individual is human.

The term "administering" or "administration" and the like, refers to providing a therapeutic agent, such as a crystalline form disclosed herein, to the subject in need of treatment. In an embodiment, the subject is a mammal. In another embodiment, the subject is a human.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±10%, including ±5%, ±1%, and +0.1% from the specified value, as such variations are appropriate to perform the disclosed methods.

Solvents can be broadly classified into polar (hydrophilic) and nonpolar (lipophilic). The polarity can be measured as the dielectric constant or the dipole moment of a compound.

Nonpolar solvents include alkanes such as pentane, hexane, heptane, and cyclohexane. Additional examples of nonpolar solvents include benzene, toluene, chloroform, and diethyl ether, petroleum ether.

Examples of polar solvents include pyridine, isopropyl acetate, dichloromethane (DCM), acetone, dimethylformamide (DMF), t-butyl alcohol, dimethylsulfoxide (DMSO), acetonitrile, isopropanol, benzyl alcohol, acetic acid, ethanol, methanol, and water.

An aprotic solvent is an organic solvent that does not contain an O—H or N—H bond; or does not exchange protons with a substance dissolved in it. Examples of aprotic solvents include dimethyl sulfoxide (DMSO), isopropyl acetate, dimethylformamide (DMF), dichloromethane (DCM), acetonitrile, acetone, methyl ethyl ketone (MEK), methyl t-butyl ether (MBTE), 2-methyltetrahydrofuran, 1,4-dioxane, ethyl acetate, tetrahydrofuran (THF), heptane, methylcyclohexane, and toluene. Additional non-limiting examples include N-methylpyrrolidone, pyridine, piperidine, dimethyl ether, and methyl dodecyl sulfoxide.

Protic solvents are those solvents that contain an O—H or N—H bond. Typical protic solvents that may be used herein include various types of glycols, e.g., tripropylene glycol methyl ether, dipropylene glycol, and propylene glycol. Examples of other protic solvents include water, ammonia, acetic acid, formic acid, and alcohols such as methanol, ethanol, isopropanol, propanol, and butanol.

Characterization of Crystalline Forms

In certain embodiments, the crystalline forms described herein are identifiable on the basis of characteristic peaks in an X-ray powder diffraction analysis. X-ray powder diffraction (XRPD) is a scientific technique using X-ray, neutron, or electron diffraction on powder, microcrystalline, or other solid materials for structural characterization of solid materials. A description of the methods used to obtain certain XRPD diffractograms in connection with the crystalline forms provided herein can be found in the Examples below. In an embodiment, the X-ray powder diffraction data provided herein is obtained by a method utilizing Cu Kα radiation.

In an aspect, provided herein is a crystalline form of 3-(5-(2-hydroxy-2-methylpropoxy)-6-methylpyrazin-2-yl)-1H-indole-7-carbonitrile.

In an embodiment, the crystalline form is anhydrous.

In another embodiment, the crystalline form is characterized by an XRPD diffractogram having peaks expressed in degrees-2-theta at angles (±0.2 degrees) of 23.8, 20.7, and 11.7.

In yet another embodiment, the crystalline form is characterized by an XRPD diffractogram having peaks expressed in degrees-2-theta at angles (±0.2 degrees) of 23.8, 20.7, 11.7, and 24.6.

In still another embodiment, the crystalline form is characterized by an XRPD diffractogram having peaks expressed in degrees-2-theta at angles (±0.2 degrees) of 23.8, 20.7, 11.7, 24.6, and 15.8.

In another embodiment, the crystalline form is characterized by an XRPD diffractogram having peaks expressed in degrees-2-theta at angles (±0.2 degrees) of 23.8, 20.7, 11.7, 24.6, 15.8, 11.5, 12.2, 12.5, 16.3, 22.5, 22.9, and 30.0.

In an embodiment, the crystalline form is characterized by an XRPD diffractogram having peaks selected from Table 1 (Form C).

TABLE 1

| Angle | d Value | Rel. Intensity |
|---|---|---|
| 8.142° | 10.84978 Å | 2.2% |
| 10.018° | 8.82193 Å | 0.3% |
| 11.495° | 7.69214 Å | 2.1% |
| 11.694° | 7.56146 Å | 30.4% |
| 12.237° | 7.22731 Å | 3.0% |
| 12.502° | 7.07472 Å | 3.0% |
| 12.843° | 6.88737 Å | 6.2% |
| 14.191° | 6.23609 Å | 0.5% |
| 15.819° | 5.59789 Å | 24.6% |
| 16.303° | 5.43251 Å | 3.0% |
| 17.623° | 5.02854 Å | 0.6% |
| 19.122° | 4.63774 Å | 0.7% |
| 19.747° | 4.49214 Å | 1.3% |
| 20.099° | 4.41425 Å | 1.4% |
| 20.714° | 4.28467 Å | 33.3% |
| 22.505° | 3.94764 Å | 5.0% |
| 22.876° | 3.88442 Å | 2.8% |
| 23.822° | 3.73227 Å | 100.0% |
| 24.584° | 3.61828 Å | 31.8% |
| 25.024° | 3.55557 Å | 0.5% |
| 25.444° | 3.49787 Å | 0.6% |
| 26.556° | 3.35384 Å | 0.8% |
| 27.134° | 3.28366 Å | 0.3% |
| 27.889° | 3.19655 Å | 0.6% |
| 28.337° | 3.14701 Å | 1.7% |
| 29.725° | 3.00312 Å | 0.6% |
| 30.029° | 2.94776 Å | 7.1% |
| 30.989° | 2.88345 Å | 0.3% |
| 32.066° | 2.78902 Å | 0.9% |
| 32.273° | 2.77163 Å | 1.6% |
| 32.842° | 2.72489 Å | 1.5% |
| 34.830° | 2.57378 Å | 0.3% |
| 35.240° | 2.54472 Å | 0.9% |
| 35.956° | 2.49572 Å | 0.6% |
| 37.378° | 2.40394 Å | 0.4% |

In another embodiment, the crystalline form has the XRPD diffractogram substantially as depicted in FIG. 1.

In another embodiment, the crystalline form has a DSC thermogram characterized by an endotherm with an onset temperature of about 179° C. In yet another embodiment, the crystalline form has a DSC thermogram characterized by an endotherm with an onset temperature of 179.3° C.

Methods of Treatment

Provided herein are methods for the treatment of a disease comprising administering a crystalline form of 3-(5-(2-hydroxy-2-methylpropoxy)-6-methylpyrazin-2-yl)-1H-indole-7-carbonitrile, or a pharmaceutical composition comprising the crystalline form and a pharmaceutically acceptable carrier.

In an aspect, provided herein is a method of treating a neurodegenerative disorder in a subject in need thereof comprising administering to the subject the crystalline form, or a pharmaceutical composition comprising the crystalline form and a pharmaceutically acceptable carrier.

In an embodiment, the neurodegenerative disorder is spinal bulbar muscular atrophy (SBMA).

In an embodiment of the methods, the crystalline form is anhydrous.

In another embodiment of the method, the crystalline form is characterized by an XRPD diffractogram having peaks expressed in degrees-2-theta at angles (±0.2 degrees) of 23.8, 20.7, and 11.7.

In yet another embodiment of the method, the crystalline form is characterized by an XRPD diffractogram having peaks expressed in degrees-2-theta at angles (±0.2 degrees) of 23.8, 20.7, 11.7, and 24.6.

In still another embodiment of the method, the crystalline form is characterized by an XRPD diffractogram having peaks expressed in degrees-2-theta at angles (±0.2 degrees) of 23.8, 20.7, 11.7, 24.6, and 15.8.

In another embodiment, the crystalline form is characterized by an XRPD diffractogram having peaks expressed in degrees-2-theta at angles (±0.2 degrees) of 23.8, 20.7, 11.7, 24.6, 15.8, 11.5, 12.2, 12.5, 16.3, 22.5, 22.9, and 30.0.

In another embodiment of the method, the crystalline form is characterized by an XRPD diffractogram having peaks selected from Table 1.

In another aspect, provided herein is a method of modulating androgen receptor (AR) activity in a subject in need thereof comprising administering to the subject the crystalline form, or a pharmaceutical composition comprising the crystalline form and a pharmaceutically acceptable carrier.

In an embodiment, the androgen receptor (AR) undergoes allosteric modulation. In another embodiment, modulating androgen receptor (AR) activity treats spinal bulbar muscular atrophy (SBMA) in the subject.

In another embodiment, the crystalline form selectively binds to the binding function-3 (BF3) domain of the androgen receptor.

In another embodiment of the method of modulated AR activity, the crystalline form is characterized by an XRPD diffractogram having peaks expressed in degrees-2-theta at angles (±0.2 degrees) of 23.8, 20.7, and 11.7.

In yet another embodiment of the method, the crystalline form is characterized by an XRPD diffractogram having peaks expressed in degrees-2-theta at angles (±0.2 degrees) of 23.8, 20.7, 11.7, and 24.6.

In another embodiment of the method, the crystalline form is characterized by an XRPD diffractogram having peaks expressed in degrees-2-theta at angles (±0.2 degrees) of 23.8, 20.7, 11.7, 24.6, and 15.8.

In still another embodiment of the method, the crystalline form is characterized by an XRPD diffractogram having peaks selected from Table 1.

In yet another aspect, provided herein is a method of treating spinal bulbar muscular atrophy (SBMA) in a subject in need thereof comprising administering to the subject a crystalline form of 3-(5-(2-hydroxy-2-methylpropoxy)-6-methylpyrazin-2-yl)-1H-indole-7-carbonitrile.

In still another aspect, provided herein is a method of treating spinal bulbar muscular atrophy (SBMA) in a subject in need thereof comprising administering to the subject a pharmaceutical composition comprising a crystalline form of 3-(5-(2-hydroxy-2-methylpropoxy)-6-methylpyrazin-2-yl)-1H-indole-7-carbonitrile and a pharmaceutically acceptable carrier.

In an embodiment of the methods, the crystalline form is anhydrous.

In an aspect, provided herein is a method of treating spinal bulbar muscular atrophy (SBMA) in a subject in need thereof comprising administering to the subject a crystalline form of 3-(5-(2-hydroxy-2-methylpropoxy)-6-methylpyrazin-2-yl)-1H-indole-7-carbonitrile, wherein the crystalline form is characterized by an XRPD diffractogram having peaks expressed in degrees-2-theta at angles (±0.2 degrees) of 23.8, 20.7, and 11.7.

In an embodiment of the methods, the crystalline form is anhydrous.

In an embodiment of the method, the crystalline form is characterized by an XRPD diffractogram having peaks expressed in degrees-2-theta at angles (±0.2 degrees) of 23.8, 20.7, 11.7, and 24.6.

In another embodiment of the method, the crystalline form is characterized by an XRPD diffractogram having peaks expressed in degrees-2-theta at angles (±0.2 degrees) of 23.8, 20.7, 11.7, 24.6, and 15.8.

In still another embodiment of the method, the crystalline form is characterized by an XRPD diffractogram having peaks selected from Table 1.

In yet another aspect, provided herein is a method of treating cancer in a subject in need thereof comprising administering to the subject the crystalline form, or a pharmaceutical composition comprising the crystalline form and a pharmaceutically acceptable carrier.

In an embodiment of the methods, the crystalline form is anhydrous.

In another embodiment of the method of treating cancer, the crystalline form is characterized by an XRPD diffractogram having peaks expressed in degrees-2-theta at angles (±0.2 degrees) of 23.8, 20.7, and 11.7.

In yet another embodiment of the method, the crystalline form is characterized by an XRPD diffractogram having peaks expressed in degrees-2-theta at angles (±0.2 degrees) of 23.8, 20.7, 11.7, and 24.6.

In another embodiment of the method, the crystalline form is characterized by an XRPD diffractogram having peaks expressed in degrees-2-theta at angles (±0.2 degrees) of 23.8, 20.7, 11.7, 24.6, and 15.8.

In still another embodiment, the crystalline form is characterized by an XRPD diffractogram having peaks selected from Table 1.

In an embodiment, the cancer is selected from hematological cancers, sarcomas, lung cancers, gastrointestinal cancers, genitourinary tract cancers, liver cancers, bone cancers, nervous system cancers, gynecological cancers, and skin cancers.

In another embodiment, the lung cancer is selected from non-small cell lung cancer (NSCLC), small cell lung cancer, bronchogenic carcinoma, squamous cell bronchogenic carcinoma, undifferentiated small cell bronchogenic carcinoma, undifferentiated large cell bronchogenic carcinoma, adenocarcinoma, bronchogenic carcinoma, alveolar carcinoma, bronchiolar carcinoma, bronchial adenoma, chondromatous hamartoma, mesothelioma, pavicellular and non-pavicellular carcinoma, bronchial adenoma, and pleuropulmonary blastoma.

In yet another embodiment, the lung cancer is non-small cell lung cancer (NSCLC). In still another embodiment, the lung cancer is adenocarcinoma.

In an embodiment, the gastrointestinal cancer is selected from esophagus squamous cell carcinoma, esophagus adenocarcinoma, esophagus leiomyosarcoma, esophagus lymphoma, stomach carcinoma, stomach lymphoma, stomach leiomyosarcoma, exocrine pancreatic carcinoma, pancreatic ductal adenocarcinoma, pancreatic insulinoma, pancreatic glucagonoma, pancreatic gastrinoma, pancreatic carcinoid tumors, pancreatic vipoma, small bowel adenocarcinoma, small bowel lymphoma, small bowel carcinoid tumors, Kaposi's sarcoma, small bowel leiomyoma, small bowel hemangioma, small bowel lipoma, small bowel neurofibroma, small bowel fibroma, large bowel adenocarcinoma, large bowel tubular adenoma, large bowel villous adenoma, large bowel hamartoma, large bowel leiomyoma, colorectal cancer, gall bladder cancer, and anal cancer.

In an embodiment, the gastrointestinal cancer is colorectal cancer.

In another embodiment, the cancer is a carcinoma. In yet another embodiment, the carcinoma is selected from pancreatic carcinoma, colorectal carcinoma, lung carcinoma, bladder carcinoma, gastric carcinoma, esophageal carcinoma, breast carcinoma, head and neck carcinoma, cervical skin carcinoma, and thyroid carcinoma.

In still another embodiment, the cancer is a hematopoietic malignancy. In an embodiment, the hematopoietic malignancy is selected from multiple myeloma, acute myelogenous leukemia, and myeloproliferative neoplasms.

In another embodiment, the cancer is a neoplasm. In yet another embodiment, the neoplasm is glioblastoma or sarcomas.

In an embodiment, the cancer is selected from the group consisting of hematological cancers, sarcomas, lung cancers, gastrointestinal cancers, genitourinary tract cancers, liver cancers, bone cancers, nervous system cancers, gynecological cancers, and skin cancers.

In an embodiment, the cancer is selected from the group consisting of pancreatic cancer, cervical cancer, colon cancer, ovarian cancer, breast cancer, pancreatic cancer, carcinoma, and adenocarcinoma.

In another embodiment, the cancer is pancreatic cancer. In yet another embodiment, the cancer is a solid tumor.

In one embodiment of the methods described herein, the subject is human.

Processes for Preparing Form C

In an aspect, provided herein is a process for preparing a crystalline form of 3-(5-(2-hydroxy-2-methylpropoxy)-6-methylpyrazin-2-yl)-1H-indole-7-carbonitrile comprising:
  a) combining 3-(5-(2-hydroxy-2-methylpropoxy)-6-methylpyrazin-2-yl)-1H-indole-7-carbonitrile with a first solvent to form a mixture;
  b) adding to the mixture seeds of crystalline 3-(5-(2-hydroxy-2-methylpropoxy)-6-methylpyrazin-2-yl)-1H-indole-7-carbonitrile;
  c) stirring the mixture;
  d) collecting solids of 3-(5-(2-hydroxy-2-methylpropoxy)-6-methylpyrazin-2-yl)-1H-indole-7-carbonitrile;
  e) washing the solids with a second solvent; and
  f) collecting and drying the crystalline form of 3-(5-(2-hydroxy-2-methylpropoxy)-6-methylpyrazin-2-yl)-1H-indole-7-carbonitrile.

In an embodiment, the first solvent is a polar solvent, and the second solvent is a nonpolar solvent.

In another embodiment, the first solvent is a nonpolar solvent, and the second solvent is a nonpolar solvent.

In yet another embodiment, the first solvent is an aprotic solvent, and the second solvent is an aprotic solvent.

In still another embodiment, the first solvent is a protic solvent, and the second solvent is an aprotic solvent.

In an embodiment, the first solvent is selected from the group consisting of acetone, 2-methyltetrahydrofuran, tetrahydrofuran, ethyl acetate, methyl ethyl ketone, isopropanol, methyl isobutyl ketone, ethanol, and isopropyl acetate, or a combination thereof.

In another embodiment, the second solvent is selected from the group consisting of heptane, methylcyclohexane, and toluene, or a combination thereof.

In yet another embodiment, the first solvent is 2-methyltetrahydrofuran, and the second solvent is heptane.

In another aspect, provided herein is a process for preparing a crystalline form of 3-(5-(2-hydroxy-2-methylpropoxy)-6-methylpyrazin-2-yl)-1H-indole-7-carbonitrile comprising:
  a) combining 3-(5-(2-hydroxy-2-methylpropoxy)-6-methylpyrazin-2-yl)-1H-indole-7-carbonitrile with a polar, aprotic solvent to form a mixture;
  b) adding to the mixture seeds of crystalline 3-(5-(2-hydroxy-2-methylpropoxy)-6-methylpyrazin-2-yl)-1H-indole-7-carbonitrile;
  c) stirring the mixture;
  d) collecting solids of 3-(5-(2-hydroxy-2-methylpropoxy)-6-methylpyrazin-2-yl)-1H-indole-7-carbonitrile;
  e) re-equilibrating the solids in the polar, aprotic solvent under a temperature cycle between about 5° C. to about 50° C.; and
  f) collecting and drying the crystalline form of 3-(5-(2-hydroxy-2-methylpropoxy)-6-methylpyrazin-2-yl)-1H-indole-7-carbonitrile.

In an embodiment, the polar, aprotic solvent in step a) is acetone. In another embodiment, the polar, aprotic solvent in step e) is acetone.

In an embodiment of the foregoing processes, the starting material is amorphous.

In another embodiment, the seeds of crystalline 3-(5-(2-hydroxy-2-methylpropoxy)-6-methylpyrazin-2-yl)-1H-indole-7-carbonitrile in step b) are characterized by an XRPD diffractogram having peaks expressed in degrees-2-theta at angles (±0.2 degrees) of 23.8, 20.7, and 11.7.

In yet another embodiment, the seeds of crystalline 3-(5-(2-hydroxy-2-methylpropoxy)-6-methylpyrazin-2-yl)-1H-indole-7-carbonitrile in step b) are characterized by an XRPD diffractogram having peaks expressed in degrees-2-theta at angles (±0.2 degrees) of 23.8, 20.7, 11.7, and 24.6.

In still another embodiment, the seeds of crystalline 3-(5-(2-hydroxy-2-methylpropoxy)-6-methylpyrazin-2-yl)-1H-indole-7-carbonitrile in step b) are characterized by an XRPD diffractogram having peaks expressed in degrees-2-theta at angles (±0.2 degrees) of 23.8, 20.7, 11.7, 24.6, and 15.8.

In another embodiment, the seeds of crystalline 3-(5-(2-hydroxy-2-methylpropoxy)-6-methylpyrazin-2-yl)-1H-indole-7-carbonitrile in step b) are characterized by an XRPD diffractogram having peaks expressed in degrees-2-theta at angles (±0.2 degrees) of 23.8, 20.7, 11.7, 24.6, 15.8, 11.5, 12.2, 12.5, 16.3, 22.5, 22.9, and 30.0.

In an embodiment, the seeds of crystalline 3-(5-(2-hydroxy-2-methylpropoxy)-6-methylpyrazin-2-yl)-1H-indole-7-carbonitrile in step b) are characterized by an XRPD diffractogram having peaks selected from Table 1 (Form C).

In another embodiment, the mixture in step c) is stirred at room temperature. In yet another embodiment, the mixture in step c) is stirred at 25° C. In yet another embodiment, the mixture in step c) is stirred for 10 days.

In still embodiment, the temperature cycle of step e) is a cycle between 5° C. to 50° C. In an embodiment, the temperature cycle of step e) is performed for three cycles.

In another embodiment, the crystalline form of 3-(5-(2-hydroxy-2-methylpropoxy)-6-methylpyrazin-2-yl)-1H-indole-7-carbonitrile in step f) is dried at about 50° C. under vacuum.

In another aspect, provided herein is a process for preparing the crystalline form disclosed herein comprising dissolving 3-(5-(2-hydroxy-2-methylpropoxy)-6-methylpyrazin-2-yl)-1H-indole-7-carbonitrile to a first solvent, adding a second solvent to form a slurry, and filtering the slurry to isolate the crystalline form of 3-(5-(2-hydroxy-2-methylpropoxy)-6-methylpyrazin-2-yl)-1H-indole-7-carbonitrile.

In an embodiment, the first solvent is selected from the group consisting of acetone, ethyl acetate, methyl tert-butyl ether (MTBE), and 2-methyltetrahydrofuran (MeTHF), or a combination thereof. In another embodiment, the first solvent is ethyl acetate. In yet another embodiment, the first solvent is acetone. In still another embodiment, the first solvent is 2-methyltetrahydrofuran (MeTHF). In an embodiment, the second solvent is heptane. In an embodiment, the second solvent is methyl tert-butyl ether (MTBE).

In another embodiment, the crystalline form is characterized by an XRPD diffractogram having peaks expressed in degrees-2-theta at angles (±0.2 degrees) of 23.8, 20.7, and 11.7.

In yet another embodiment, the crystalline form is characterized by an XRPD diffractogram having peaks expressed in degrees-2-theta at angles (±0.2 degrees) of 23.8, 20.7, 11.7, and 24.6.

In still another embodiment, the crystalline form is characterized by an XRPD diffractogram having peaks expressed in degrees-2-theta at angles (±0.2 degrees) of 23.8, 20.7, 11.7, 24.6, and 15.8.

In another embodiment, the crystalline form is characterized by an XRPD diffractogram having peaks expressed in degrees-2-theta at angles (±0.2 degrees) of 23.8, 20.7, 11.7, 24.6, 15.8, 11.5, 12.2, 12.5, 16.3, 22.5, 22.9, and 30.0.

In an embodiment, the crystalline form is characterized by an XRPD diffractogram having peaks selected from Table 1 (Form C).

Pharmaceutical Compositions

In an aspect, provided herein is a pharmaceutical composition comprising a crystalline form provided herein and a pharmaceutically acceptable carrier.

In an embodiment, the pharmaceutical composition comprises a crystalline form that is substantially free from other crystalline forms.

In another embodiment, the crystalline form is characterized by an XRPD diffractogram having peaks expressed in degrees-2-theta at angles (±0.2 degrees) of 23.8, 20.7, and 11.7.

In yet another embodiment, the crystalline form is characterized by an XRPD diffractogram having peaks expressed in degrees-2-theta at angles (±0.2 degrees) of 23.8, 20.7, 11.7, and 24.6.

In another embodiment, the crystalline form is characterized by an XRPD diffractogram having peaks expressed in degrees-2-theta at angles (±0.2 degrees) of 23.8, 20.7, 11.7, 24.6, and 15.8.

In still another embodiment, the crystalline form is characterized by an XRPD diffractogram having peaks selected from Table 1.

The pharmaceutical compositions can be formulated for oral, intravenous, intramuscular, subcutaneous or parenteral administration for the therapeutic or prophylactic treatment of Kennedy's disease.

The pharmaceutical preparations disclosed herein can be prepared in accordance with standard procedures and are administered at dosages that are selected to reduce, prevent or eliminate disease. See, for example, Remington's Pharmaceutical Sciences, Mack Publishing Company, Easton, PA and Goodman and Gilman's "The Pharmaceutical Basis of Therapeutics," Pergamon Press, New York, NY, the contents of which are incorporated herein by reference, for a general description of the methods for administering various agents for human therapy.

The pharmaceutical compositions described herein can comprise a crystalline form disclosed herein in association with one or more nontoxic, pharmaceutically acceptable carriers and/or diluents and/or adjuvants and/or excipients.

For oral or parenteral administration, the crystalline form disclosed herein can be mixed with conventional pharmaceutical carriers and excipients and used in the form of tablets, capsules, elixirs, suspensions, syrups, wafers and the like. The compositions comprising a crystalline form disclosed herein can contain from about 0.1% to about 99% by weight of the active compound, such as from about 10% to about 30%.

For oral use, solid formulations such as tablets and capsules are useful. Sustained release or enterically coated preparations can also be devised. For pediatric and geriatric applications, one embodiment provides suspensions, syrups and chewable tablets. For oral administration, the pharmaceutical compositions are in the form of, for example, a tablet, capsule, suspension or liquid.

The pharmaceutical compositions can be made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, fillers, lubricants, disintegrants, or acceptable wetting agents. Oral liquid preparations generally are in the form of aqueous or oily solutions, suspensions, emulsions, syrups or elixirs.

The pharmaceutical compositions disclosed herein can be placed in a pharmaceutically acceptable carrier and are delivered to a recipient subject (e.g., a human) in accordance with known methods of drug delivery. In general, the methods of delivering the pharmaceutical compositions in vivo utilize art-recognized protocols for delivering the agent with the only substantial procedural modification being the substitution of a crystalline form of the present disclosure for the drugs in the art-recognized protocols.

Administration/Dosage/Formulations

In another aspect, provided herein is a pharmaceutical composition comprising a crystalline form provided herein, together with a pharmaceutically acceptable carrier.

Actual dosage levels of the active ingredients in the pharmaceutical compositions discussed herein may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the crystalline form, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed crystalline form at levels lower than that required in order to achieve the desired therapeutic effect and gradually increase the dosage until the desired effect is achieved.

In particular embodiments, it is especially advantageous to formulate the crystalline form in dosage unit form for ease of administration and uniformity of dosage.

"Dosage unit form," as used herein, refers to physically discrete units suited as unitary dosages for the patients to be treated; each unit containing a predetermined quantity of the disclosed compound calculated to produce the desired therapeutic effect in association with the required pharmaceutical vehicle. The dosage unit forms of the crystalline form disclosed herein are dictated by and directly dependent on (a) the unique characteristics of the disclosed compound and the particular therapeutic effect to be achieved, and (b) the limitations inherent in the art of compounding/formulating such a disclosed compound for the treatment of Kennedy's disease (SBMA) in a patient.

In one embodiment, the crystalline form provided herein is formulated using one or more pharmaceutically acceptable excipients or carriers. In one embodiment, the pharmaceutical compositions comprise a therapeutically effective amount of the disclosed crystalline form and a pharmaceutically acceptable carrier.

In some embodiments, the dose of a disclosed compound is from about 1 mg to about 1,000 mg. In some embodiments, a dose of the disclosed compound used in compositions described herein is less than about 1,000 mg, or less than about 800 mg, or less than about 600 mg, or less than about 500 mg, or less than about 300 mg, or less than about 200 mg, or less than about 100 mg, or less than about 50 mg, or less than about 20 mg, or less than about 10 mg. For example, a dose is about 10 mg, 20 mg, 25 mg, 30 mg, 40 mg, 50 mg, 60 mg, 70 mg, 80 mg, 90 mg, 100 mg, 120 mg, 140 mg, 160 mg, 180 mg, 200 mg, 220 mg, 240, 260 mg, 280 mg, 300 mg, 350 mg, 400 mg, 450 mg, 500 mg, 550 mg, or about 600 mg.

Routes of administration of any of the compositions disclosed herein include oral, nasal, rectal, intravaginal, parenteral, buccal, sublingual or topical. The compound for use provided herein may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example, an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compound may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings of the present disclosure as set forth.

EXAMPLES

The disclosure is further illustrated by the following examples, which should not be construed as further limiting. The practice of the present disclosure will employ, unless otherwise indicated, conventional techniques of organic synthesis, cell biology, cell culture, and molecular biology, which are within the skill of the art.

Synthesis of 3-(5-(2-hydroxy-2-methylpropoxy)-6-methylpyrazin-2-yl)-1H-indole-7-carbonitrile Step 1: To a degassed mixture of 5-iodo-3-methyl-2-[2-methyl-2-(oxan-2-yloxy)propoxy]pyrazine (150 mg, 0.38 mmol) and tert-butyl 7-cyano-3-(4,4,5,5-tetramethyl-1,3,2-dioxaborolan-2-yl)indole-1-carboxylate (140 mg, 0.38 mmol) in dioxane (2 mL) and water (0.2 mL) were added potassium carbonate (105 mg, 0.76 mmol) and [1,1-bis(diphenylphosphino)ferrocene]dichloropalladium(II) (27 mg, 0.04 mmol) at room temperature. The mixture was stirred at 100° C. for 2 hours. The reaction mixture was diluted using water and extracted with ethyl acetate. The organic combined layers were washed with brine, dried over anhydrous sodium sulfate, filtered and concentrated under vacuum. The residue was purified by flash column chromatography with 0-35% ethyl acetate in petroleum ether to afford 3-[6-methyl-5-[2-methyl-2-(oxan-2-yloxy)propoxy]pyrazin-2-yl]-1H-indole-7-carbonitrile (67 mg, 43%) as a white solid. MS m/z 407.1 [M+1]+.

Step 2: To a solution of 3-[6-methyl-5-[2-methyl-2-(oxan-2-yloxy)propoxy]pyrazin-2-yl]-1H-indole-7-carbonitrile (62 mg, 0.15 mmol) in dichloromethane (2.1 mL) was added trifluoroacetic acid (0.7 mL) at room temperature. The mixture was stirred at room temperature for 3 hours. The mixture was concentrated under vacuum. The residue was purified by reverse phase flash column chromatography with 10-80% acetonitrile in water (10 mmol/L ammonium bicarbonate) to afford 3-[5-(2-hydroxy-2-methylpropoxy)-6-methylpyrazin-2-yl]-1H-indole-7-carbonitrile (21.3 mg, 43%) as a white solid. $^1$H NMR (400 MHz, DMSO-d$_6$) δ 12.35 (s, 1H), 8.73 (d, J=8.0 Hz, 1H), 8.56 (s, 1H), 8.19 (d, J=2.4 Hz, 1H), 7.69-7.67 (m, 1H), 7.28 (t, J=8.0 Hz, 1H), 4.70 (br, 1H), 4.10 (s, 2H), 2.54 (s, 3H), 1.24 (s, 6H); MS (ESI) calcd for $C_{18}H_{18}N_4O_2$ [M+1]$^+$, 323.1; found, 323.0.

Biological Assay

LNCaP cells expressing ARR2PB-FireflyLuc and CMV-RenillaLuc were treated with indicated concentrations of the test compound, enzalutamide (negative control), or DHT (positive control)+/−0.5 nM DHT for 48 h at 37° C. Fluorescent signals were read with the ImageXpress Micro Confocal System. Remaining activity (antagonist mode) was calculated as % Remaining Activity=100×[(Read$_{sample}$−LC$_{ave}$)/(HC$_{ave}$−LC$_{ave}$)] where HC is cells treated with 0.5 nM DHT only and LC is cells treated with 10 uM enzalutamide+0.5 nM DHT. Activation (agonist mode) was calculated as % Activation=100×[(ReadSample−LC$_{ave}$)/(HC$_{ave}$−LC$_{ave}$)] where HC is cells treated with 1 uM DHT and LC is cells treated with DMSO. Dose response curves and IC$_{50}$ values were calculated using non-linear regression analysis in XLfit. 3-(5-(2-hydroxy-2-methylpropoxy)-6-methylpyrazin-2-yl)-1H-indole-7-carbonitrile was found to have an IC$_{50}$ value of 50 nM.

Analytical Methods for Polymorph Studies

Unless otherwise indicated, X-ray powder diffraction (XRPD) was performed on a Bruker D8 Advance diffractometer in reflection mode using collimated Cu Kα radiation operating at 40 kV, 40 mA. Scans were run from 2-40 degrees 2-theta with a step size of 0.02 degrees and a scan time of 0.3 second per step.

Differential Scanning Calorimetry (DSC) was conducted on a TA Discovery 2500 with a Tzero pan and Tzero hermetic lid with a pin hole of 0.7 mm in diameter. DSC analysis was performed by ramping 10° C./min or 20° C./min from 30 to 250° C. or 0 to 250° C.

Thermal gravimetric analysis (TGA) was conducted on Discovery 5500 or Q5000 with a start temperature at ambient conditions (below 35° C.) and a final temperature of 300° C. (or abort next segment if weight <80% (w/w)) with a heat 10° C./min.

Nuclear magnetic resonance (NMR) analysis was run on a Bruker Avance-AV 400M at a frequency of 400 MHz for eight scans.

Dynamic vapor sorption (DVS) was performed on an Intrinsic, Advantage or Adventure with an oven temperature of 25° C. using water as a solvent. The sample mass was about 5-10 mg using the following method:

Cycle: 40-0-95-0-40% RH
Stage Step: 10%
Equilibrium: 0.002 dm/dt (%/min)
Minimum dm/dt stability duration: 60 min
Maximum dm/dt stage time: 360 min.

Analysis of Polymorphs 3-(5-(2-hydroxy-2-methylpropoxy)-6-methylpyrazin-2-yl)-1H-indole-7-carbonitrile free form shows complicated polymorphic behaviors. In total, 15 forms were identified to be polymorphs or pseudo-polymorphs of the free form, including seven anhydrates, Forms A, C, H, J, K. L and O; four hydrates, Forms B, F, M and N; and three solvates, Forms D, E and I. In addition, a metastable form, Form G, and an amorphous form were also obtained.

Figure 7:
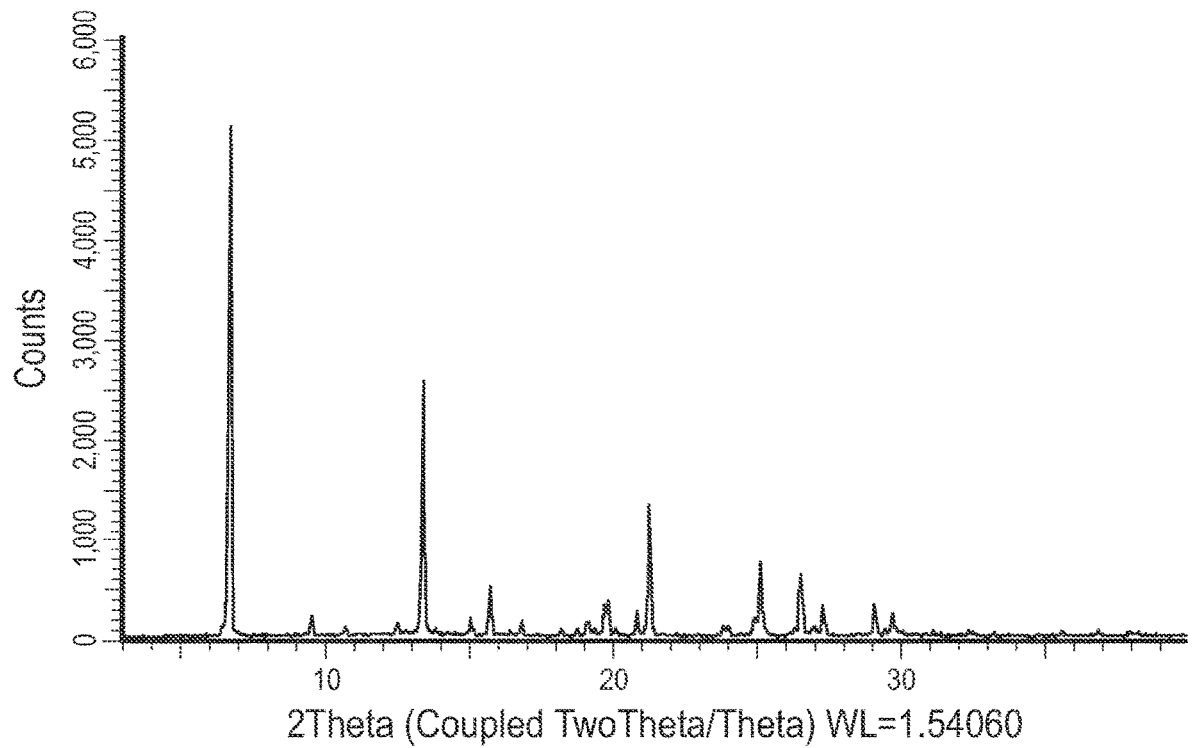
FIG. 7 shows the XRPD diffractogram of 3-(5-(2-hydroxy-2-methylpropoxy)-6-methylpyrazin-2-yl)-1H-indole-7-carbonitrile anhydrate Form A.

Form A is an anhydrate. It was obtained from many solvent systems by equilibration, slow cooling, fast cooling, evaporation, vapor diffusion and antisolvent addition experiments. Form A is of high crystallinity. DSC shows a melting point peak at T$_{onset}$ of 170.2° C. and then follows another endothermic peak at T$_{onset}$ of 178.9° C. TGA shows about 0.2% weight loss at about 160° C. $^1$H-NMR shows no detectable residual solvent. Form A converts to Form C at both 25° C. and 50° C., suggesting that Form A is thermodynamically less stable than Form C. The XRPD diffractogram of Form A is shown in FIG. 7.

Figure 8:
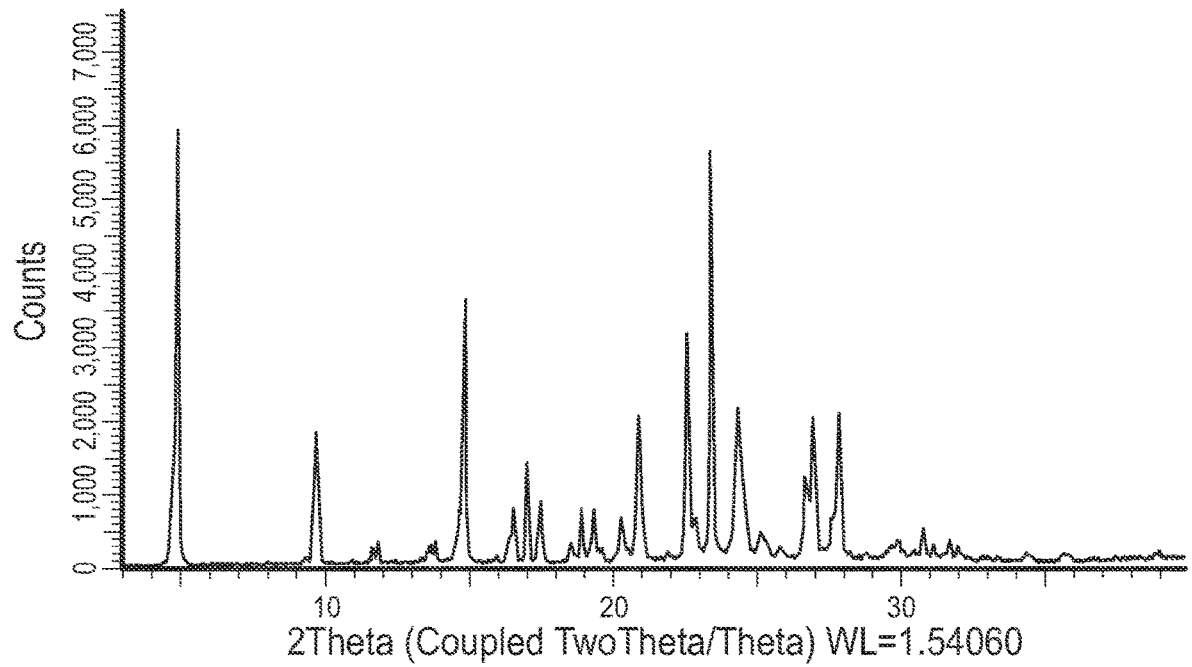
FIG. 8 shows the XRPD diffractogram of 3-(5-(2-hydroxy-2-methylpropoxy)-6-methylpyrazin-2-yl)-1H-indole-7-carbonitrile hydrate Form B.

Form B is a hydrate. It was only obtained from methanol system by temperature cycle, slow cooling, slow evaporation and fast evaporation. Form B is of high crystallinity. DSC shows a dehydration peak at T$_{onset}$ at 16.7° C. with an enthalpy of about 22 J/g and a small exothermic peak at T$_{onset}$ of 130.5° C. Then 2 un-resolved endothermic peaks at T$_{onset}$ of 170.2° C. and T$_{onset}$ of 173.1° C., respectively. After that, it shows two small unresolved endothermic peaks at T$_{onset}$ of 177.8° C. and T$_{onset}$ of 179.0° C., respectively. TGA shows about 2.1% weight loss at about 150° C. KF shows it contains about 3.8% water by weight, equivalent to 0.7 water molecule. $^1$H-NMR shows no detectable residual solvent. Form B shows reversible dehydration-hydration behavior. It converts to Form K after dehydration and Form K reverts back to Form B after exposure to 25° C. in 40-70% RH for 6 days. Form B is a metastable hydrate and it converts to anhydrate Form C in the whole range of water activity (0≤a·w≤1). The XRPD diffractogram of Form B is shown in FIG. 8.

Figure 2:
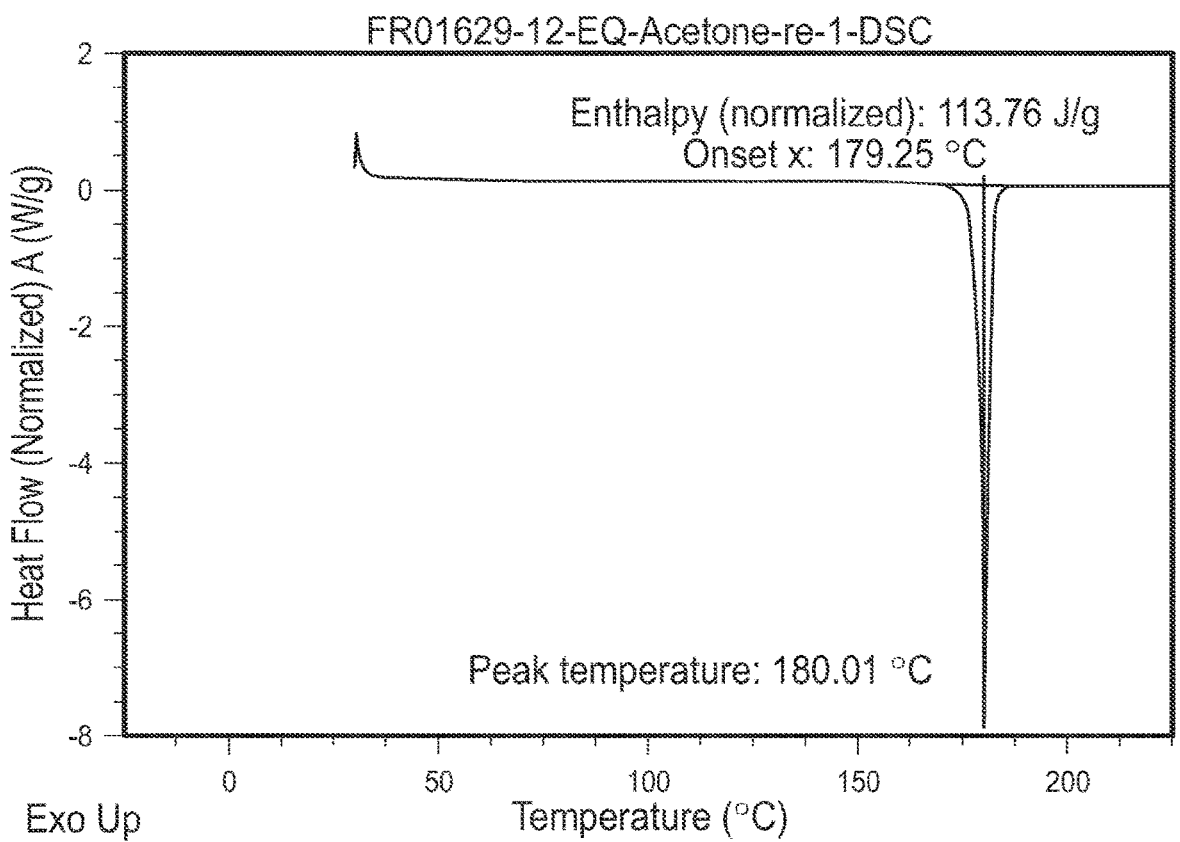
FIG. 2 shows the DSC thermogram of crystalline 3-(5-(2-hydroxy-2-methylpropoxy)-6-methylpyrazin-2-yl)-1H-indole-7-carbonitrile anhydrate Form C.

Form C is an anhydrate. It was obtained from some of solvent systems by equilibration, slow cooling, fast cooling, slow evaporation and vapor diffusion. Form C is of high crystallinity. DSC shows a melting peak at T$_{onset}$ of 179.3° C. with an enthalpy of about 114 J/g (FIG. 2). TGA shows about 0.8% weight loss at about 150° C. (FIG. 3). 1H-NMR shows no detectable residual solvent (FIG. 4). Form C is the most stable polymorph compared to the other polymorph forms described herein. Competitive equilibration experiments show that Form C is thermodynamically stable anhydrate both at 25° C. and at 50° C. Water activity study shows that Form C is stable in the whole range of water activity (0≤a·w≤1). The XRPD diffractogram of Form C is shown in FIG. 1.

Figure 9:
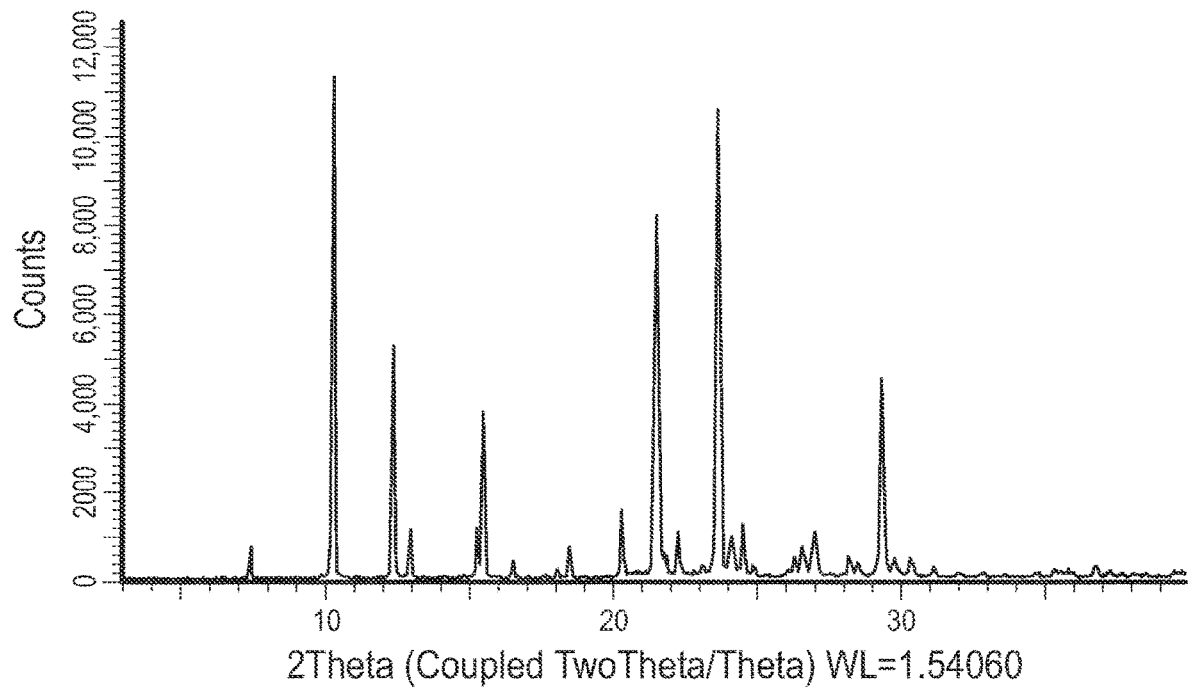
FIG. 9 shows the XRPD diffractogram of 3-(5-(2-hydroxy-2-methylpropoxy)-6-methylpyrazin-2-yl)-1H-indole-7-carbonitrile solvate Form D.

Form D is a 1,4-dioxane solvate. It was only obtained from 1,4-dioxane system by equilibration, slow cooling, fast cooling, slow evaporation, fast evaporation, and vapor diffusion experiments. Form D is of high crystallinity. DSC shows two desolvation peaks at T$_{onset}$ of 88.0° C. with an enthalpy of about 27 J/g and at T$_{onset}$ of 138.6° C. with an enthalpy of about 41 J/g, suggesting that 1,4-dioxane molecules have two types of intermolecular interaction formats with the API molecule in crystal structure of Form D. Then it melts at T$_{onset}$ of 179.1° C. with an enthalpy of about 111 J/g. TGA shows about 9.1% weight loss at about 130° C. and about 2.8% weight loss from about 130° C. to 160° C. $^1$H-NMR shows 0.5 equiv. (13.6%) 1,4-dioxane residue by weight. Form D converts to Form C after desolvation. The XRPD diffractogram of Form D is shown in FIG. 9.

Form E is an EtOH/water solvate. It was obtained from ethanol system by fast evaporation experiments. Form E is of high crystallinity. DSC shows a desolvation/dehydration peak at T$_{onset}$ of 80.4° C. with an enthalpy of about 8 J/g and un-resolved melting peaks at T$_{onset}$ of 165.2° C. and 170.2° C., respectively. This un-resolved melting peak is followed with a recrystallization peak at T$_{onset}$ of 173.1° C. After recrystallization, it shows a melting point at T$_{onset}$ of 177.9°

Figure 10:
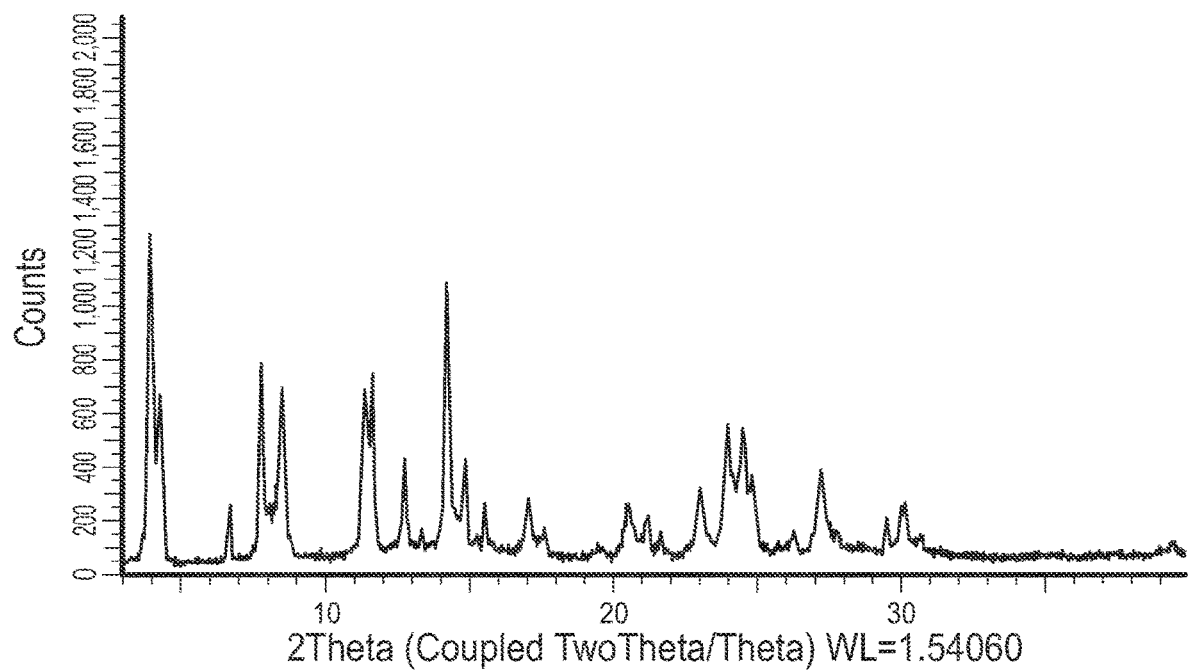
FIG. 10 shows the XRPD diffractogram of 3-(5-(2-hydroxy-2-methylpropoxy)-6-methylpyrazin-2-yl)-1H-indole-7-carbonitrile solvate Form E.

C. that is close to the melting of Form C. TGA shows about 2.1% weight loss at about 120° C. $^1$H-NMR shows 1.4% EtOH by weight. KF shows that it contains about 0.6% water by weight. Form E converts to physical mixture of Form F and Form G after heating to 100° C. by TGA and cooled to room temperature. The XRPD diffractogram of Form E is shown in FIG. 10.

Figure 11:
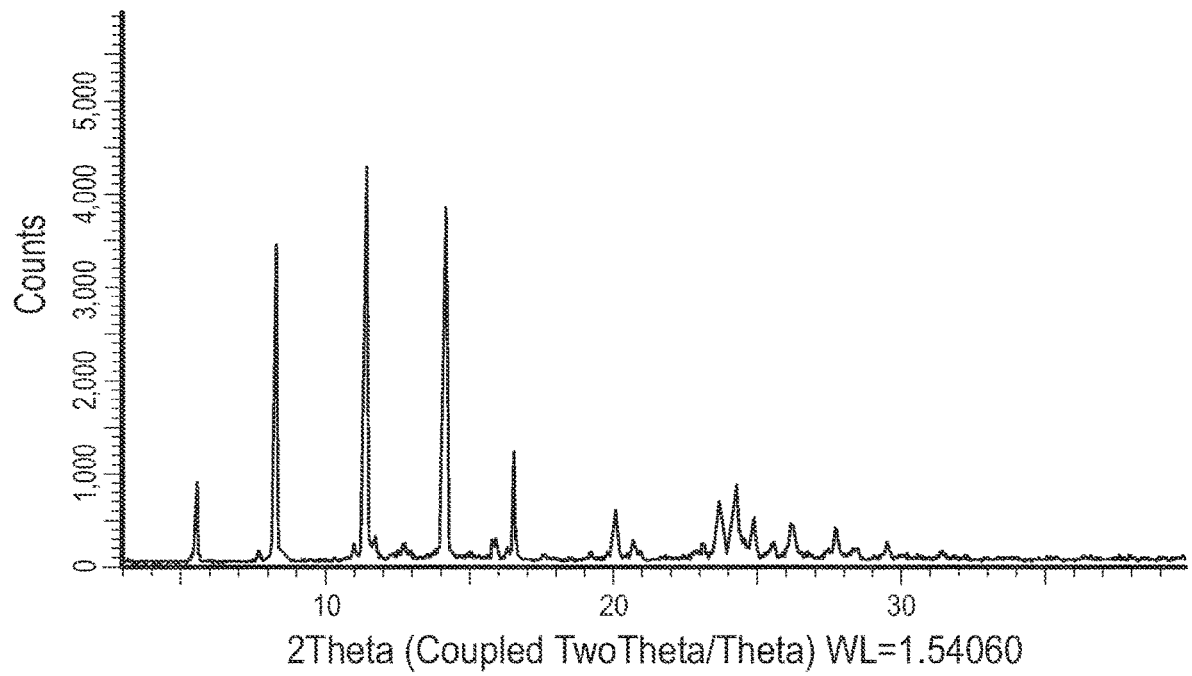
FIG. 11 shows the XRPD diffractogram of 3-(5-(2-hydroxy-2-methylpropoxy)-6-methylpyrazin-2-yl)-1H-indole-7-carbonitrile hydrate Form F.

Form F is a hydrate. It was obtained from THF or MEK system by fast evaporation experiments. Form F is of high crystallinity. DSC shows 2 un-resolved melting peaks at $T_{onset}$ of 163.2° C. and 169.7° C. combined with a recrystallization peak at $T_{onset}$ of 171.7° C. After recrystallization, it shows a melting point at $T_{onset}$ of 177.9° C. that is close to the melting of Form C. TGA shows about 0.5% weight loss at about 140° C. and about 0.7% weight loss from about 140° C. to 180° C. 1H-NMR shows 0.5% THF residue by weight. KF shows it contains about 1.7% water by weight. Form F is a metastable hydrate and it converts to Form C in the whole range of water activity (0≤a·w·≤1). The XRPD diffractogram of Form F is shown in FIG. 11.

Figure 12:
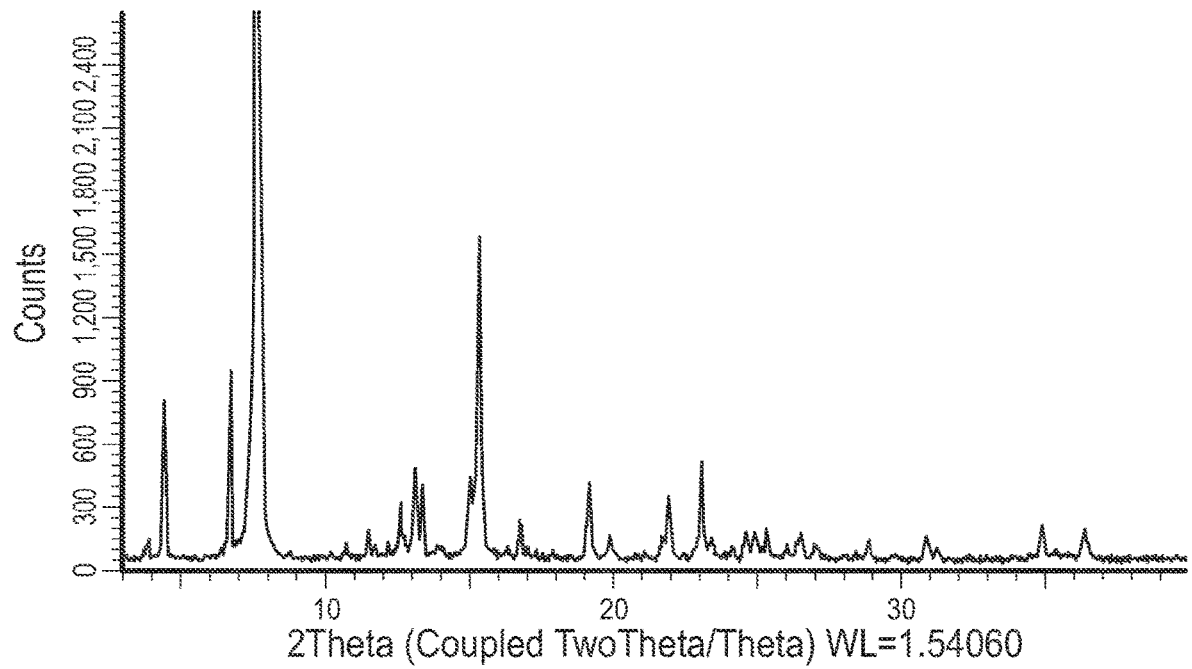
FIG. 12 shows the XRPD diffractogram of 3-(5-(2-hydroxy-2-methylpropoxy)-6-methylpyrazin-2-yl)-1H-indole-7-carbonitrile Form G.

Form G is a metastable form. It was obtained from DMSO/water system by anti-solvent addition experiments. Form G is of high crystallinity. It converts to anhydrate Form H after equilibration in DMSO/water system at 25° C. for 6 days. The XRPD diffractogram of Form G is shown in FIG. 12.

Figure 13:
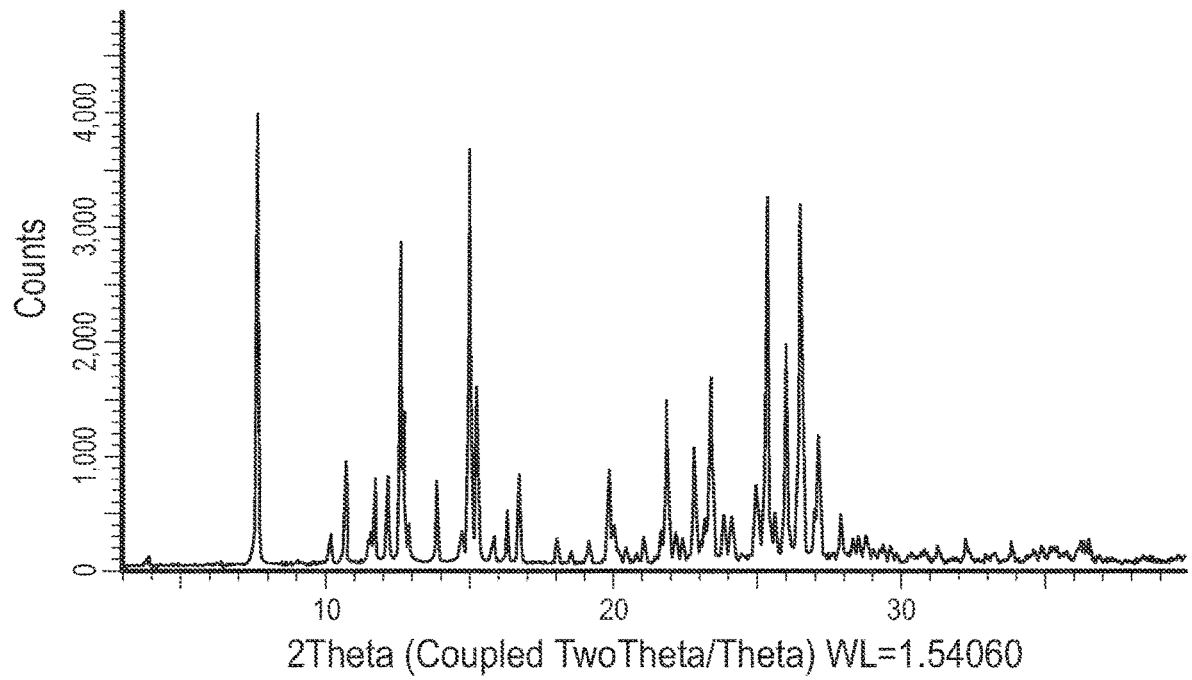
FIG. 13 shows the XRPD diffractogram of 3-(5-(2-hydroxy-2-methylpropoxy)-6-methylpyrazin-2-yl)-1H-indole-7-carbonitrile anhydrate Form H.

Form H is an anhydrate. It was obtained from acetone or acetone/water (v:v=20:80) by slow cooling experiments. Form H is of high crystallinity. DSC shows un-resolved melting peaks at $T_{onset}$ of 169.3° C. and 173.2° C., respectively. After that, it shows a small endothermic peak at $T_{onset}$ of 179.2° C. TGA shows about 1.2% weight loss at about 150° C. $^1$H-NMR shows no detectable residual solvent. Form H is a metastable anhydrate. It converts to Form C at both 25° C. and 50° C., suggesting that Form H is thermodynamically less stable than Form C. The XRPD diffractogram of Form H is shown in FIG. 13.

Figure 14:
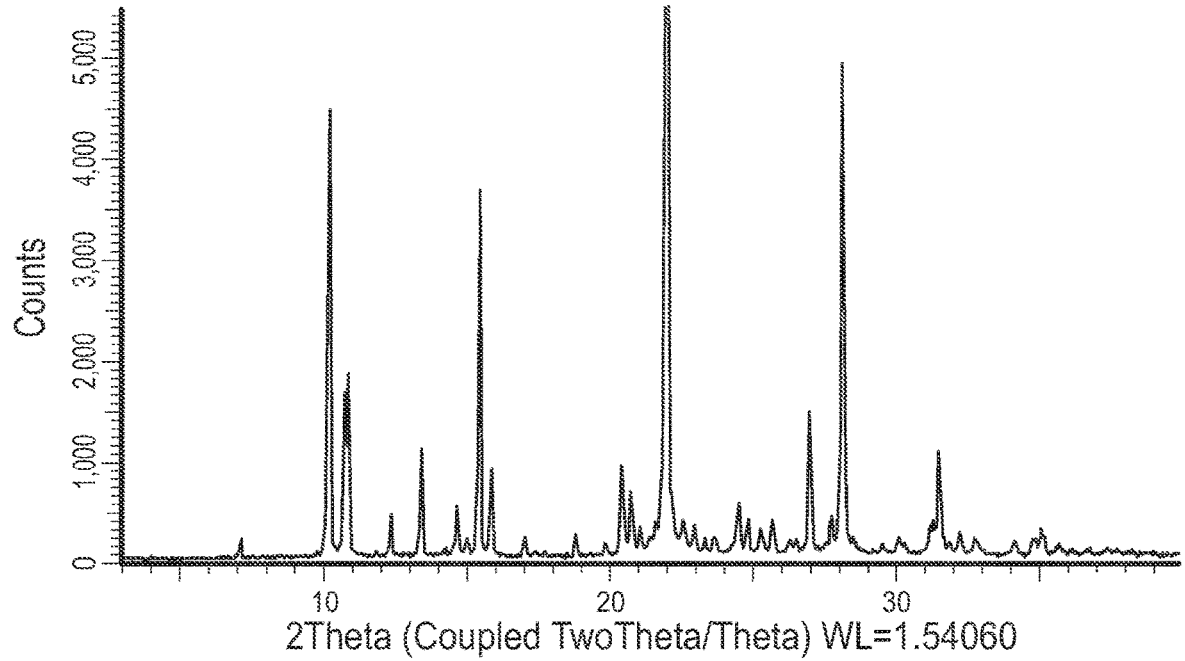
FIG. 14 shows the XRPD diffractogram of 3-(5-(2-hydroxy-2-methylpropoxy)-6-methylpyrazin-2-yl)-1H-indole-7-carbonitrile solvate Form I.

Form I is a THF solvate. It was obtained from THF/heptane system by anti-solvent addition experiments. Form I is of high crystallinity. DSC shows a desolvation peak at $T_{onset}$ of 92.8° C. with an enthalpy of about 73 J/g. Then it melts at $T_{onset}$ of 178.5° C. with an enthalpy of about 114 J/g. TGA shows about 10.0% weight loss at about 130° C. $^1$H-NMR shows 0.5 equiv. (10.1%) THF residue by weight. Form I converted to physical mixture of Form C, Form N and an unknown peak after heating to 140° C. by TGA and cooled to room temperature. The XRPD diffractogram of Form I is shown in FIG. 14.

Figure 15:
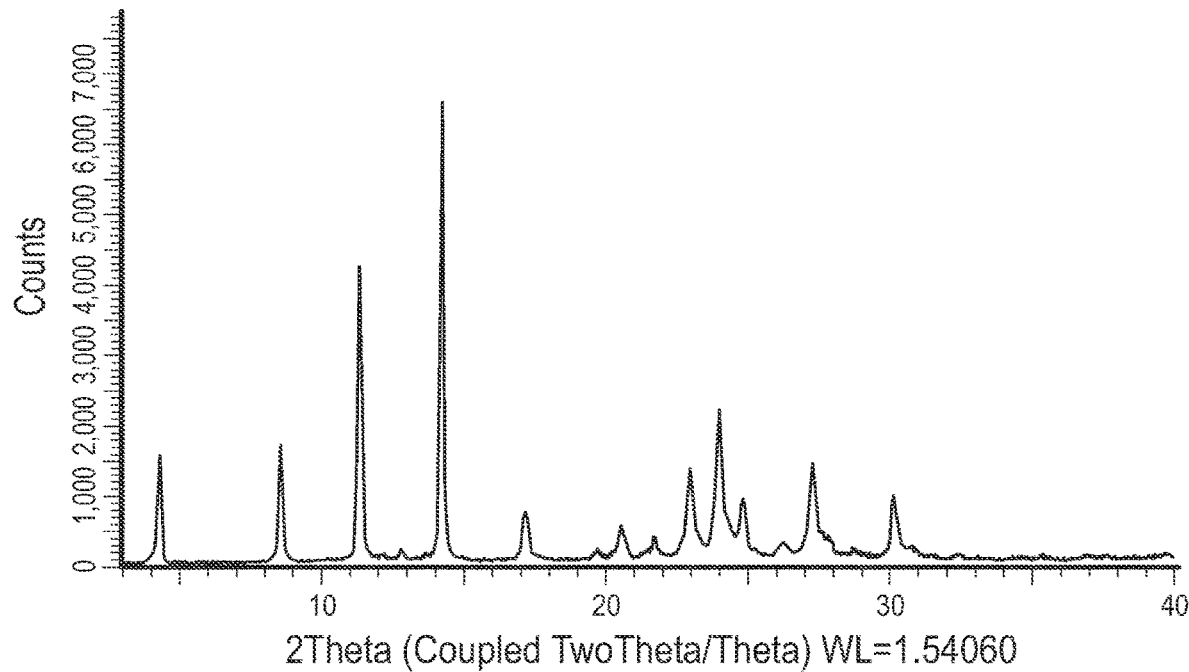
FIG. 15 shows the XRPD diffractogram of 3-(5-(2-hydroxy-2-methylpropoxy)-6-methylpyrazin-2-yl)-1H-indole-7-carbonitrile anhydrate Form J.

Form J is an anhydrate. It was obtained by heat-cool DSC. Form J is of high crystallinity. DSC shows a small exothermic event with an onset of 94.0° C., a melting point peak at $T_{onset}$ of 172.1° C. and then follows another endothermic peak at $T_{onset}$ of 177.4° C. TGA shows about 0.6% weight loss at about 150° C. $^1$H-NMR shows no detectable residual solvent. Form J is a metastable anhydrate and it converts to Form C at both 25° C. and at 50° C., suggesting that Form J is thermodynamically less stable than Form C. The XRPD diffractogram of Form J is shown in FIG. 15.

Figure 16:
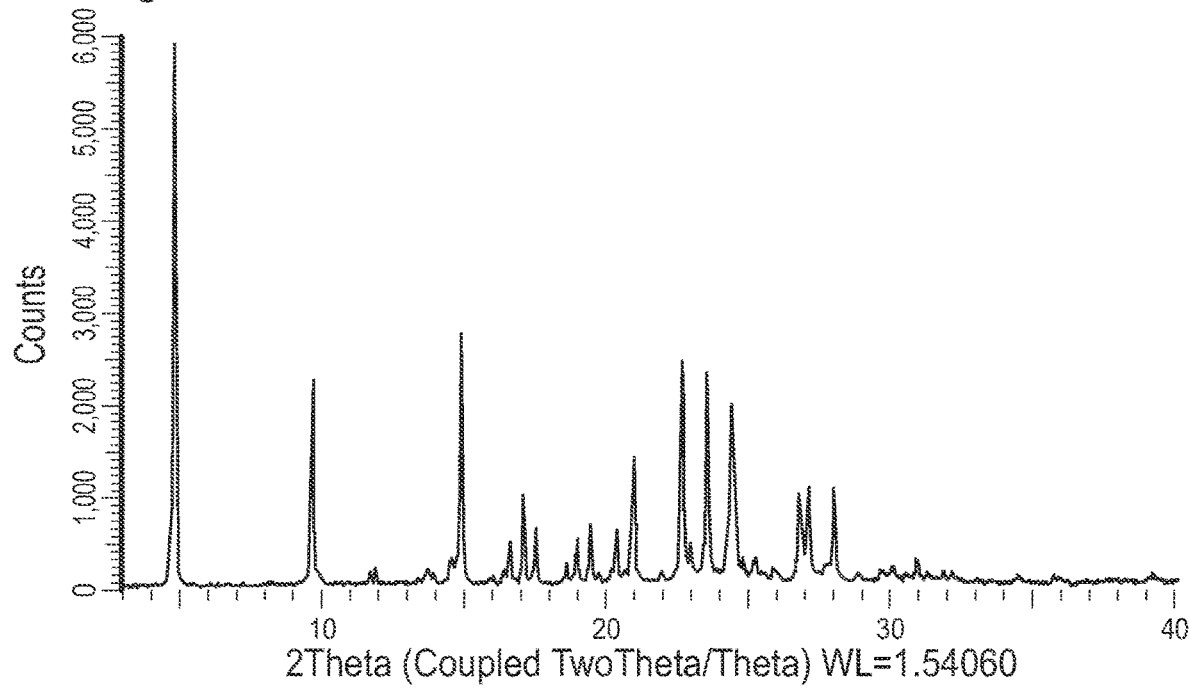
FIG. 16 shows the XRPD diffractogram of 3-(5-(2-hydroxy-2-methylpropoxy)-6-methylpyrazin-2-yl)-1H-indole-7-carbonitrile anhydrate Form K.

Form K is an anhydrate. It was obtained from methanol system from equilibration, fast cooling experiments and dehydration of Form B. Form K is of high crystallinity. DSC shows two unresolved melting peaks at $T_{onset}$ of 168.7° C. and 171.9° C. combined with a recrystallization peak at $T_{onset}$ of 173.4° C. After recrystallization, it shows two unresolved melting peaks at $T_{onset}$ of 177.3° C. and 178.8° C., respectively. Form K is unstable and it converts to hydrate Form B after exposure to 25° C./92% RH for 6 days. The XRPD diffractogram of Form K is shown in FIG. 16.

Figure 17:
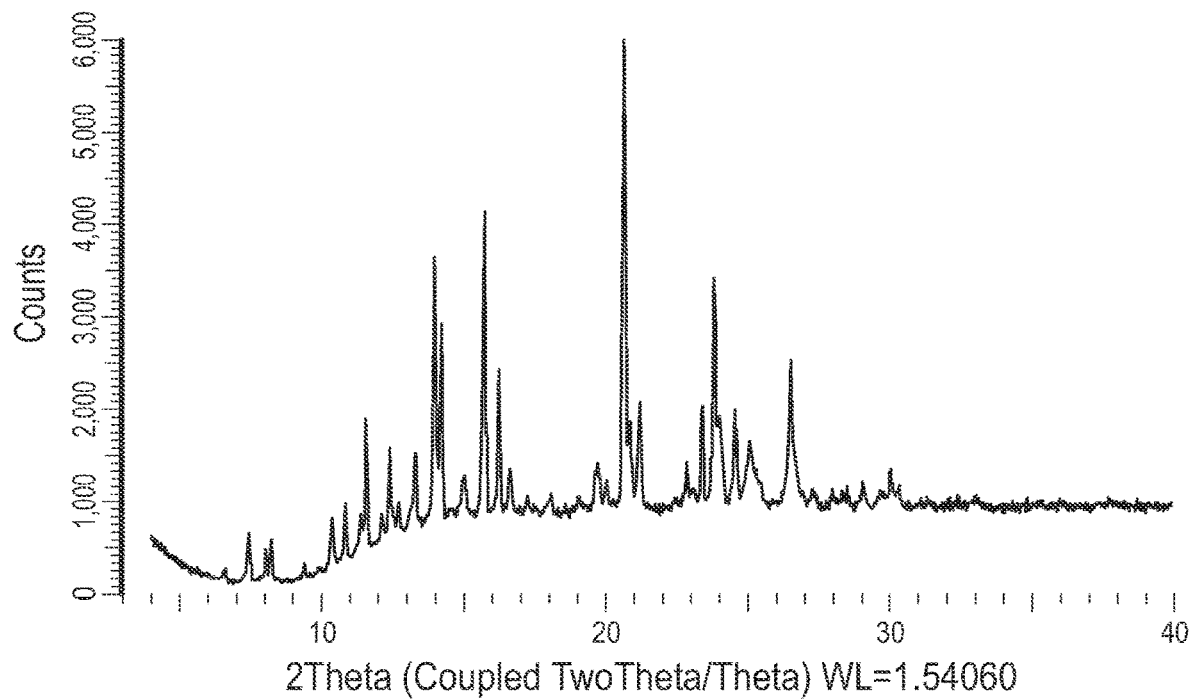
FIG. 17 shows the XRPD diffractogram of 3-(5-(2-hydroxy-2-methylpropoxy)-6-methylpyrazin-2-yl)-1H-indole-7-carbonitrile anhydrate Form L.

Form L is an anhydrate. It was obtained after heated Form B to 160° C. and cooled to room temperature. Form L is of high crystallinity. Based on DSC thermogram and VT-XRPD results, Form K converts to Form L after melting and re-crystallization. Form L melts at $T_{onset}$ of 173.5° C. with an enthalpy of about 86 J/g. Form L is a metastable anhydrate, and it converts to Form C at both 25° C. and 50° C., suggesting that Form L is thermodynamically less stable than Form C. The XRPD diffractogram of Form L is shown in FIG. 17.

Figure 18:
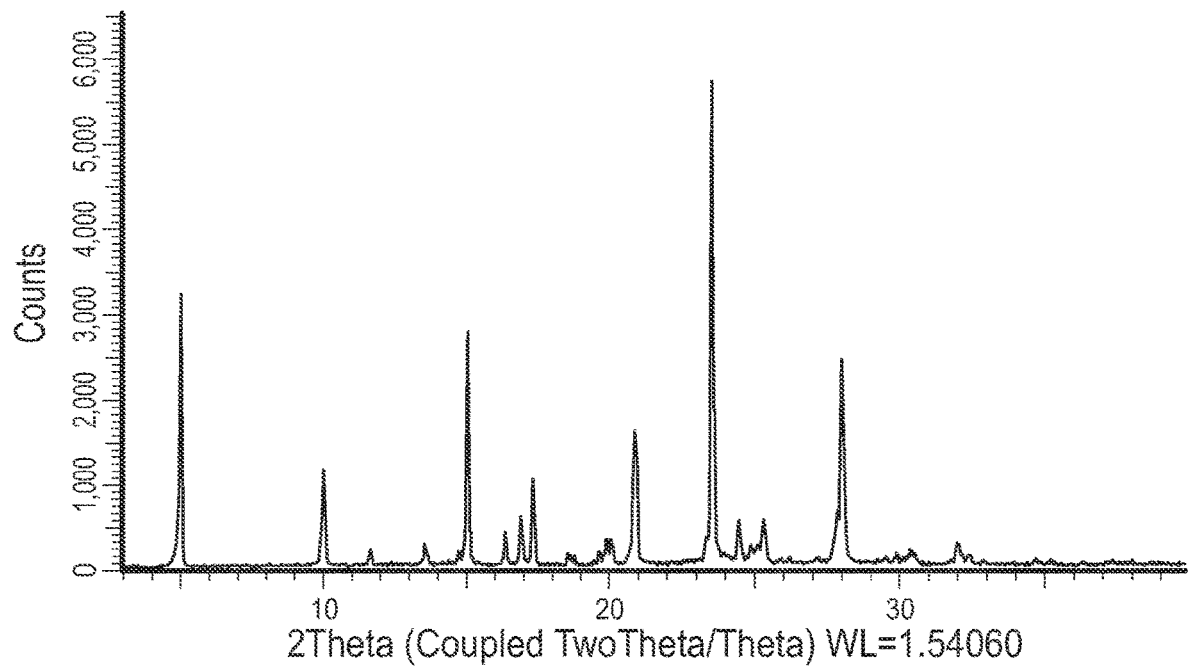
FIG. 18 shows the XRPD diffractogram of 3-(5-(2-hydroxy-2-methylpropoxy)-6-methylpyrazin-2-yl)-1H-indole-7-carbonitrile Form M.

Form M is an intermediate crystalline form. It was obtained from methanol system by equilibration. Form M is of high crystallinity. It converts to Form B after equilibration in MeOH at 25° C. for another 1 day. Therefore, full characterization data of Form M is not available. The XRPD diffractogram of Form M is shown in FIG. 18.

Figure 19:
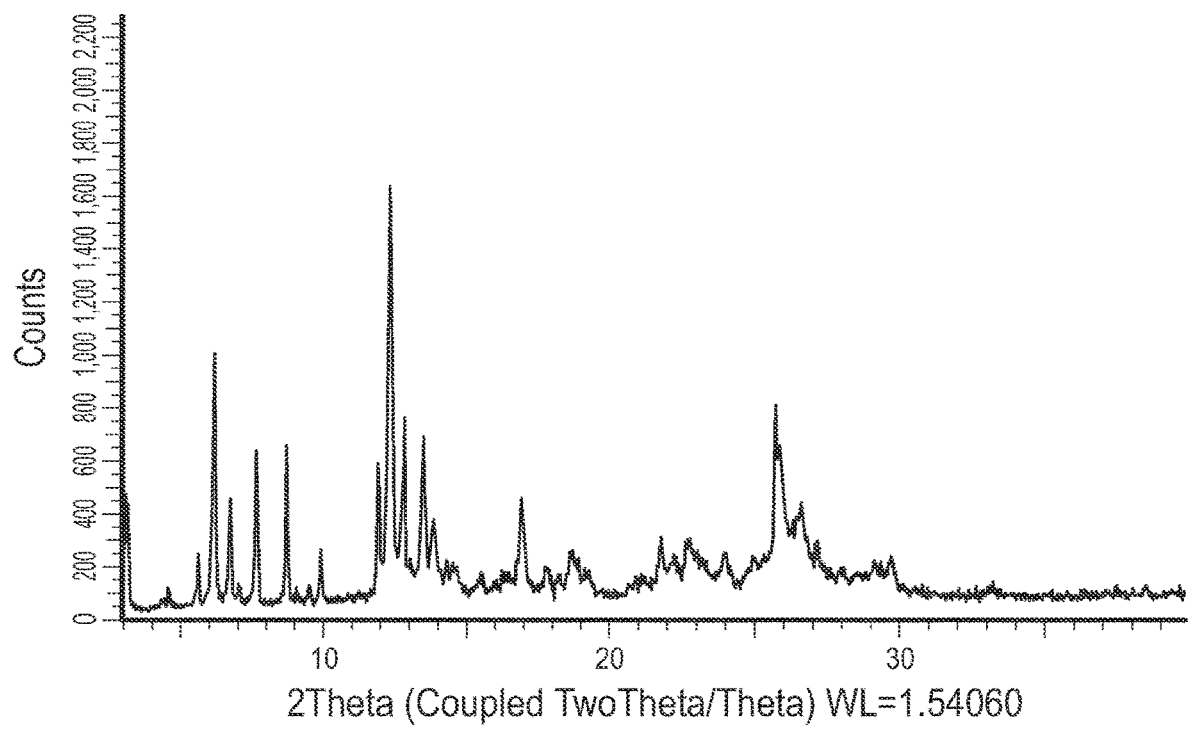
FIG. 19 shows the XRPD diffractogram of 3-(5-(2-hydroxy-2-methylpropoxy)-6-methylpyrazin-2-yl)-1H-indole-7-carbonitrile hydrate Form N.

Form N is a hydrate. It was obtained from exposing amorphous form to 25° C./92% RH in an open container for 3 days. Form N is of high crystallinity. DSC shows a dehydration peak at $T_{onset}$ of 47.1° C., an exothermic peak at $T_{onset}$ of 81.1° C. and an endothermic peak at $T_{onset}$ of 128.5° C. with an enthalpy of about 11 J/g. Then it melts at $T_{onset}$ of 171.6° C. with an enthalpy of about 76 J/g. Two small endothermic peaks with $T_{onset}$ of 177.3° C. and 178.8° C. are shown after melting. KF shows it contains about 8.7% water by weight, equivalent to 1.5 water molecule. Form N is a metastable hydrate and it converts to Form C in the whole range of water activity (0≤a·w·≤1). The XRPD diffractogram of Form N is shown in FIG. 19.

Figure 6:
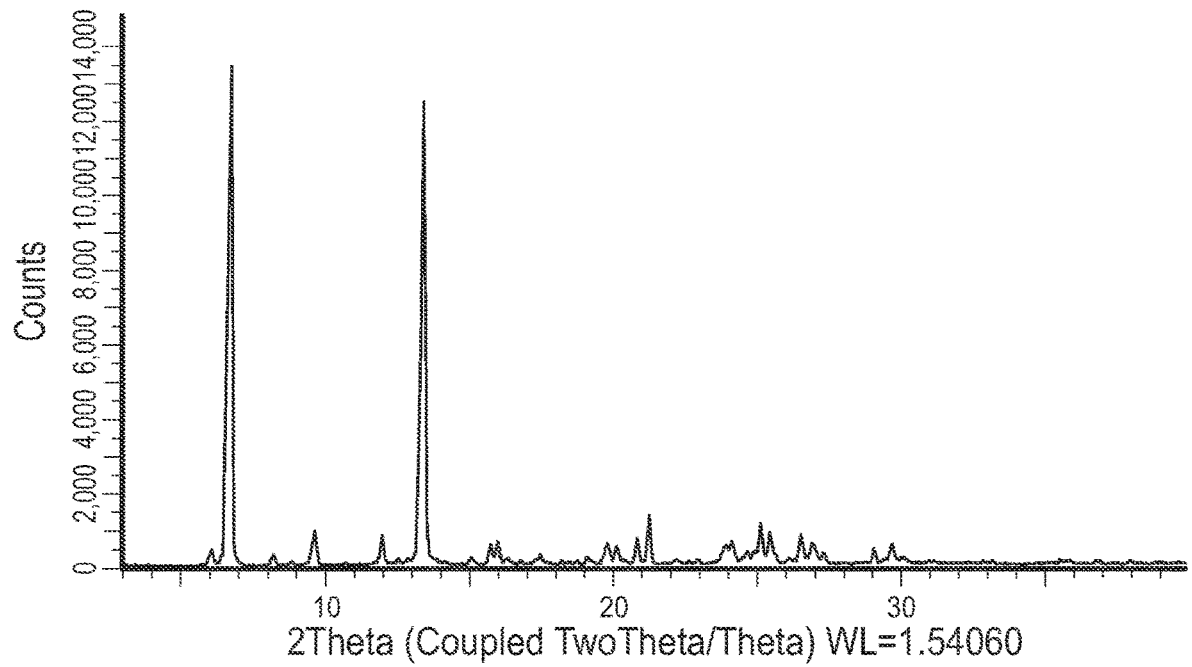
FIG. 6 shows the XRPD diffractogram of 3-(5-(2-hydroxy-2-methylpropoxy)-6-methylpyrazin-2-yl)-1H-indole-7-carbonitrile Form O.

Form O is an anhydrate. It was obtained from temperature cycle, slow evaporation and fast evaporation in some solvent systems. Form O is of high crystallinity. DSC shows unresolved melting peaks at $T_{onset}$ of 170.1° C. and 178.5° C., respectively. TGA shows about 0.7% weight loss at about 180° C. 1H-NMR shows no detectable residual solvent. The XRPD of Form O is shown in FIG. 6.

An amorphous form was prepared by heat-cool TGA using the free form. The amorphous form crystallized to Form N after exposure to high humidity.

Table 2 outlines the screening conditions of the polymorphs discussed above.

TABLE 2

Summary of screening conditions of polymorphs

| Polymorphs | Screening experiments |
|---|---|
| Form A, anhydrate | From most of solvent systems by equilibration, slow cooling, fast cooling, slow evaporation, fast evaporation, vapor diffusion and antisolvent addition experiments |
| Form B, hydrate | From methanol system by temperature cycle, slow cooling, slow evaporation and fast evaporation |
| Form C, anhydrate | From most of solvent systems by equilibration, slow cooling, fast cooling, slow evaporation and vapor diffusion. |
| Form D, solvate | From 1,4-dioxane system by equilibration, slow cooling, fast cooling, slow evaporation, fast evaporation, and vapor diffusion experiments. |
| Form E, solvate | From ethanol system by fast evaporation experiments |
| Form F, hydrate | From THF or MEK system by fast evaporation experiments |
| Form G | From DMSO/Water system by antisolvent experiments |
| Form H, anhydrate | From acetone or acetone/water (v:v = 20:80) by slow cooling experiments |
| Form I, solvate | From THF/Heptane system by antisolvent experiments for 6 days |

TABLE 2-continued

Summary of screening conditions of polymorphs

| Polymorphs | Screening experiments |
|---|---|
| Form J, anhydrate | By heat-cool DSC |
| Form K, anhydrate | From methanol system from equilibration, fast cooling experiments and Form B after dehydration |
| Form L, anhydrate | After heated Form B to 160° C. and cooled to room temperature |
| Form M | From methanol system by equilibration |
| Form N, hydrate | Exposure amorphous form to 25° C./92% RH in an open container for 3 days |
| Form O | From water system by temperature cycle, IPAc system by slow evaporation, ACN system by fast evaporation |
| Amorphous form | Prepared by heat-cool TGA using 3-(5-(2-hydroxy-2-methylpropoxy)-6-methylpyrazin-2-yl)-1H-indole-7-carbonitrile free form |

Preparation of Form C

Form C was prepared using the following procedure:

200 mg of free form was weighed into a 4 mL glass vial. 200 μL of acetone was added into the vial under stirring at 25° C. About 3 mg of Form C seeds was added into the solution. After stirring at 25° C. for 10 days, solids were collected by suction filtration and then dried at 25° C. under vacuum for about 4 hours. The dry solids were re-equilibrated in 100 μL of acetone under a temperature cycle between 5° C. to 50° C. at a heating/cooling rate of 0.1° C./min. After 3 cycles, solids were collected by suction filtration at 5° C. and then dried at 50° C. under vacuum for about 2 hours. 136 mg of Form C was obtained as an off-white solid in 67% yield.

Alternative Preparation of Form C

Purification: A total of 11.5 kg of 3-(5-(2-hydroxy-2-methylpropoxy)-6-methylpyrazin-2-yl)-1H-indole-7-carbonitrile was purified from crude 3-(5-(2-hydroxy-2-methylpropoxy)-6-methylpyrazin-2-yl)-1H-indole-7-carbonitrile (17.0 kg) in one batch using 2-MeTHF/n-heptane. The desired product was isolated as a white solid with 100% HPLC purity.

Purification was prepared using the following procedure:
1. Charge 3-(5-(2-hydroxy-2-methylpropoxy)-6-methylpyrazin-2-yl)-1H-indole-7-carbonitrile (1×(0.95-1.05×)) into a first reactor.
2. Charge 2-MeTHF (3.3-3.9 volumes) into the reactor.
3. Adjust the reactor to 45-55° C.
4. Stir the solution in the reactor for 0.5-2 h at 45-55° C. to get a clear solution.
5. Decolor organic layer by filtration through a charcoal filter at 45-55° C. for 5-15 hr.
8. Take sample for analysis.
9. Transfer the liquor into a second reactor through cartridge filter.
10. Rinse the first reactor and charcoal filter with 2-MeTHF (1.5-3.0 volumes) twice.
11. Transfer the rinse liquor into the second reactor through cartridge filter.
12. Adjust the second reactor to 55-65° C.
13. Concentrate the second reactor to 2-4 volumes below 65° C. under vacuum.
14. Charge 2-MeTHF (1.0-5.0 volumes) into the second reactor through spray ball.
15. Adjust the second reactor to 55-65° C.
16. Charge n-heptane (1.5-2.8 volumes) into the second reactor at 55-65° C. over 1-5 h.
17. Charge the seed (0.001-0.10 volumes) into the second reactor at 55-65° C.
18. Stir the second reactor for 1-4 hr at 55-65° C.
22. Take sample for analysis.
23. Charge n-heptane (4.1-9.0 volumes) into the second reactor at 55-65° C. over 7-12 h.
24. Stir the second reactor for 1-5 hr at 55-65° C.
25. Adjust the second reactor to 20-30° C. over 7-12 hr.
26. Stir the second reactor for 5-15 h at 20-30° C.
27. Take sample for analysis.
28. Filter and wash cake with 2-MeTHF/n-heptane solution (1.5-2.9 volumes) twice.
29. Take sample of mother liquor for analysis.
30. Take sample of wet cake for analysis.
31. Dry the wet cake at 40-50° C. for 15-35 hr.
32. Take sample for analysis.
33. Sieve and package.
34. Obtain 3-(5-(2-hydroxy-2-methylpropoxy)-6-methylpyrazin-2-yl)-1H-indole-7-carbonitrile.
35. Take sample for analysis.

Interrelationship of Polymorphs

Figure 5:
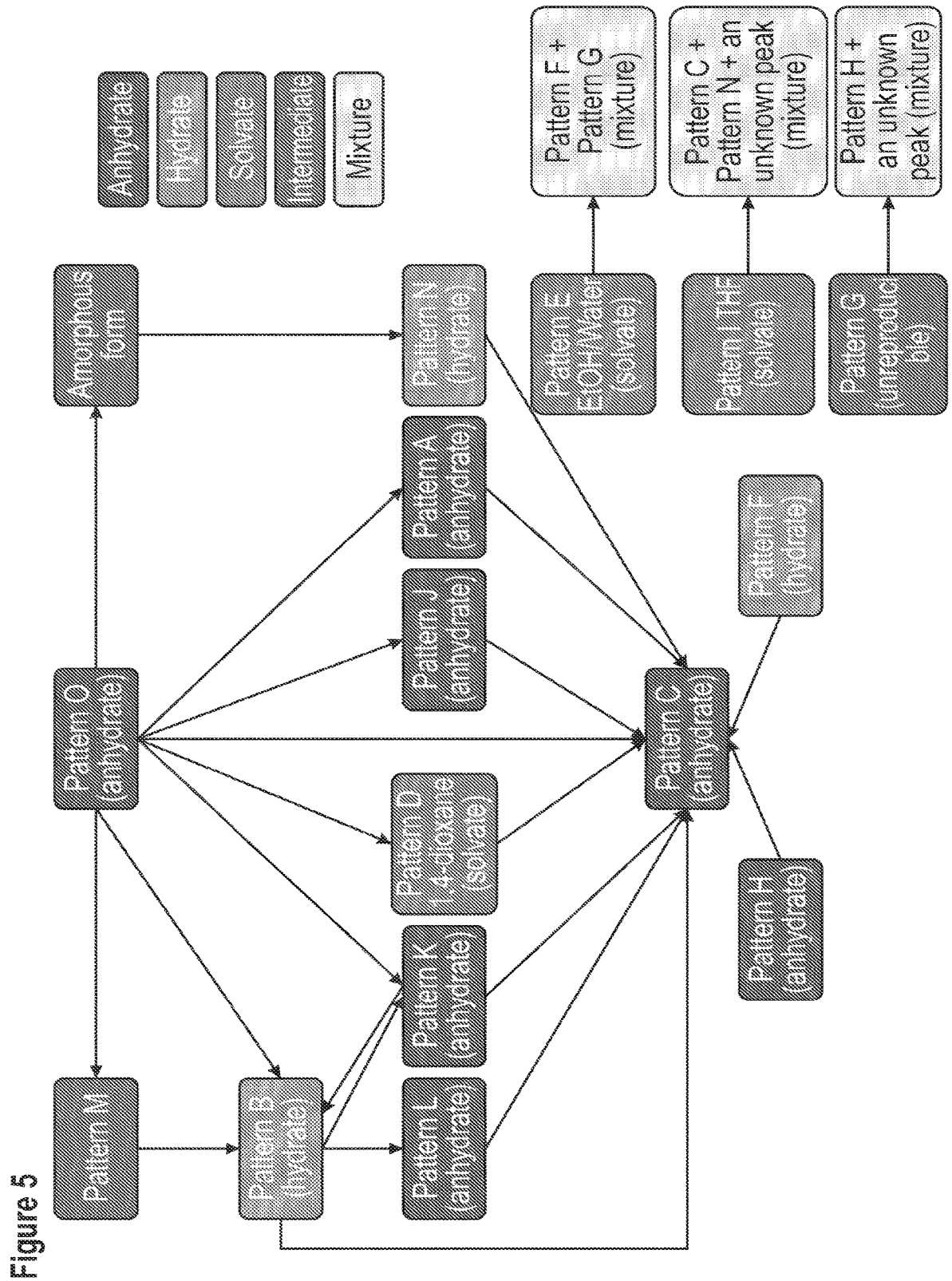
FIG. 5 is a schematic diagram of the interconversion relation of polymorphs of 3-(5-(2-hydroxy-2-methylpropoxy)-6-methylpyrazin-2-yl)-1H-indole-7-carbonitrile.

The interconversion relation of polymorphs identified is outlined in FIG. 5.

Relative stability of the anhydrate Forms A, C, H and J was investigated with competitive equilibration experiments. Form C was obtained in all selected solvents at both 25° C. and 50° C. except in MeOH, where Form B was obtained. Intermediate crystalline form, Form M, was obtained from methanol as a wet cake and further converted to Form B readily once exposed to the air. The presence of intermediate Form M affects the competitive equilibration experiments and cannot reflect the real thermodynamic relationships among anhydrates in methanol. In other solvent systems selected, Form C is the most stable form.

Relative stability of the anhydrates Forms C, K and L was investigated with competitive equilibration experiments. Form C was obtained in IPAc both at 25° C. and at 50° C.

Form C is therefore the thermodynamically stable anhydrate both at 25° C. and at 50° C.

Relative stability of anhydrate Form C, hydrate Form B, and hydrate Form F was investigated by competitive water activity experiments. Relative stability the anhydrate Form C and the hydrate Form N was also investigated by water activity experiments in acetone/water solvent mixture (a·w·=0.95). Results show that Form C is the thermodynamically stable form in the whole range of water activity (0≤a·w·≤1). Thus, anhydrate Form C is the optimal polymorph of 3-(5-(2-hydroxy-2-methylpropoxy)-6-methylpyrazin-2-yl)-1H-indole-7-carbonitrile free form.

Competitive Equilibration

To determine relative stability of anhydrates, competitive equilibration experiments were conducted in different solvent systems.

About 2 mg of each anhydrate was added to 0.3-0.4 mL saturated solutions of selected solvents. Obtained suspensions were stirred at 25° C. for 3-10 days, respectively. Solid parts (wet cakes) were isolated by centrifugation filtration and investigated by XRPD. The results are shown in Table 3.

TABLE 3

Competitive equilibration experiments

Samples: Form A + Form C + Form J + Form H

| | | XRPD | | |
|---|---|---|---|---|
| No. | Solvents | 25° C. for 4 days | 50° C. for 4 days | Comments |
| 1 | IPAc | Form C | Form C | // |
| 2 | 2-MeTHF/ | Form C | Form C | // |

TABLE 3-continued

Competitive equilibration experiments

| No. | Solvents | 25° C. for 10 days | 50° C. for 10 days | Comments |
|---|---|---|---|---|
| 3 | MEK | Form C | Form C | // |
| 4 | MeOH | Form M | Physical mixture of Form B and Form M | Starting material of Forms A, C, J, and H in methanol for 4 days: XRPD: Form M Starting material in methanol for 5 days: XRPD: Form B DSC: Dehydration from 30° C. 173.5° C., 78J/g Un-resolved melting peak: 178.2° C.; 179.3° C. |
| 5 | Acetonitrile | Form C | Form C | // |

Samples: Form A + Form C + Form J + Form H

XRPD

| No. | Solvents | 25° C. for 10 days | 50° C. for 10 days | Comments |
|---|---|---|---|---|
| 4 | MeOH | Form B | Form K | 25° C.: DSC: Dehydration from 30° C.; Un-resolved onset: 170.2° C., 173.2° C.; Re-crystallization: 175.2° C.; Un-resolved melting onset: 178.1° C., 179.2° C. 50° C.: DSC: Onset: 172.9° C., 75J/g; Un-resolved onset: 177.7° C., 179.0° C. |

Samples: Form C + Form K + Form L

XRPD

| No. | Solvents | 25° C. for 3 days | 50° C. for 3 days | Comments |
|---|---|---|---|---|
| 6 | IPAc | Form C + peaks of Form A | Form C | // |
|  | 25° C. for 6 days | // | // |  |
| 7 | IPAc | Form C | // | // |

// = No comments.

Physicochemical Characteristics

The physicochemical characteristics of Form C are summarized in Table 4.

TABLE 4

Physicochemical characteristics

Figure 3:
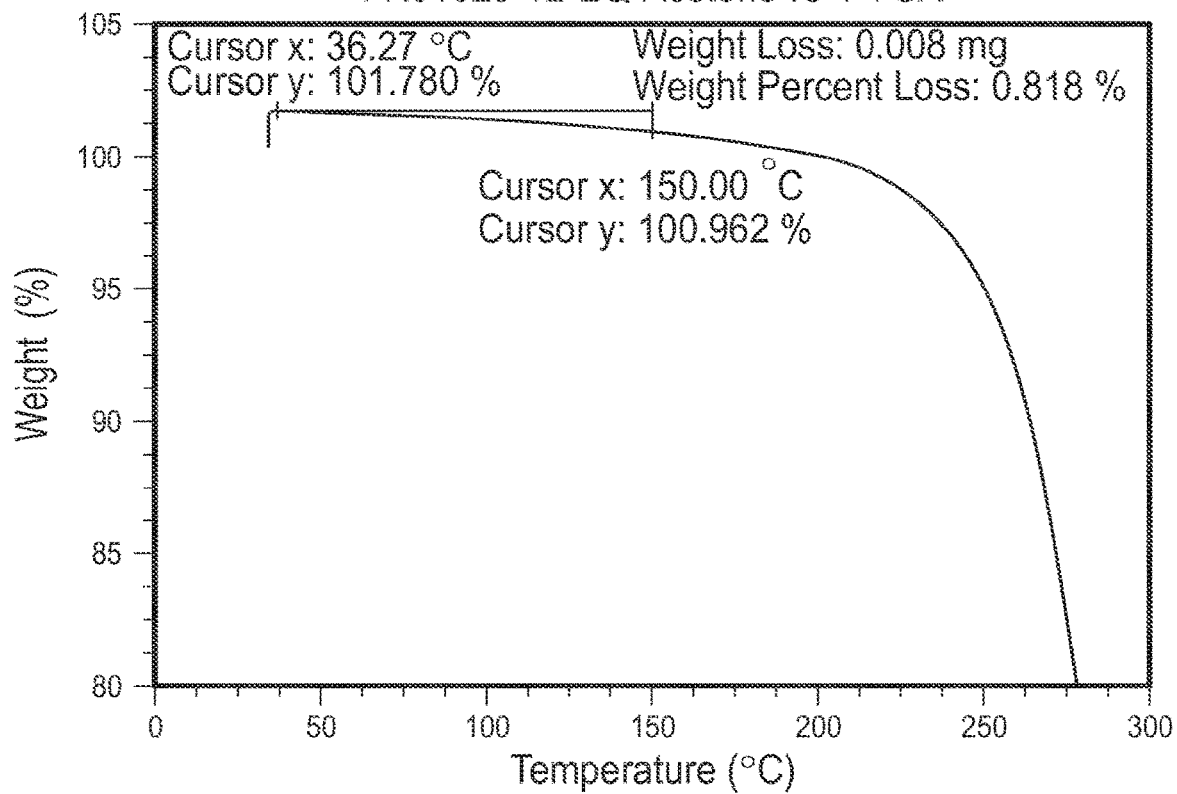
FIG. 3 shows the TGA thermogram of 3-(5-(2-hydroxy-2-methylpropoxy)-6-methylpyrazin-2-yl)-1H-indole-7-carbonitrile anhydrate Form C.
Figure 4:
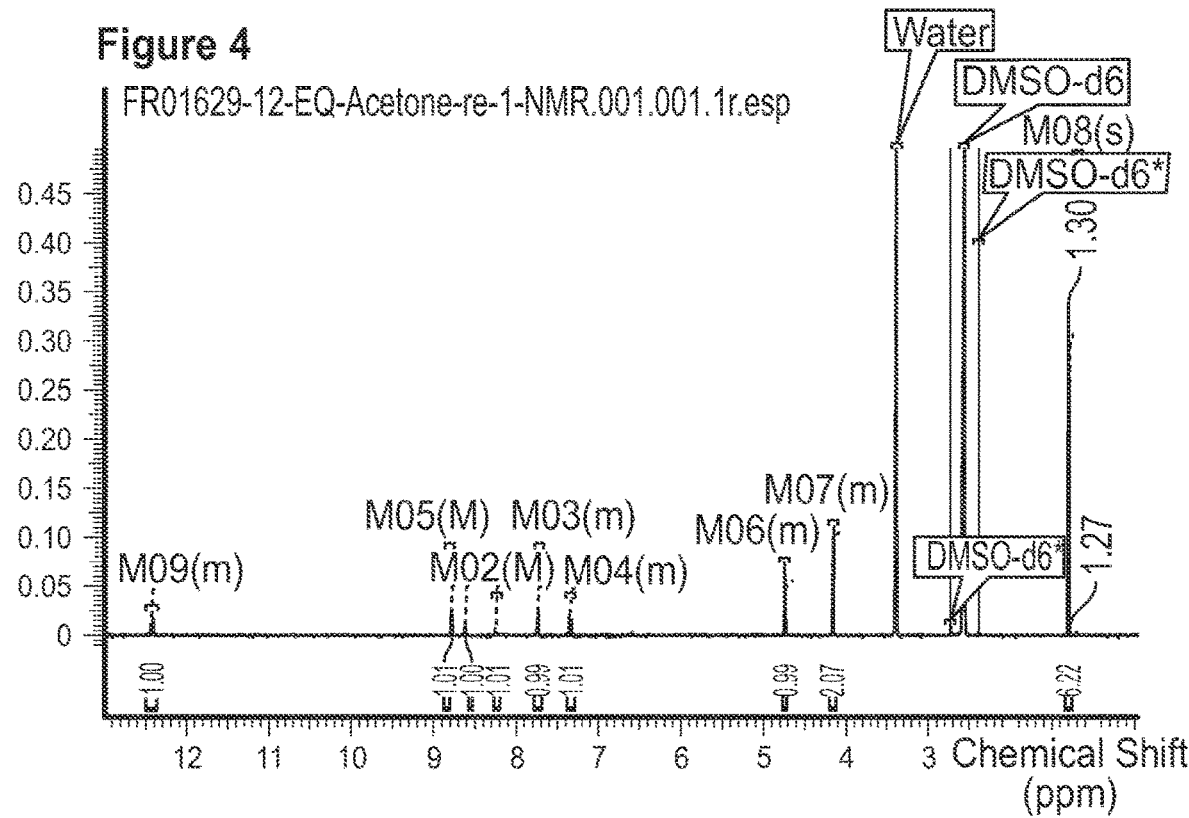
FIG. 4 shows the $^1$H NMR spectrum of 3-(5-(2-hydroxy-2-methylpropoxy)-6-methylpyrazin-2-yl)-1H-indole-7-carbonitrile anhydrate Form C.

| Polymorph Parameters | Form C Method | Results |
|---|---|---|
| Purity | HPLC | 99.2% |
| X-ray diffraction | 3-40° (2 theta) | Highly crystalline-shown in FIG. 1 |
| Melting onset and enthalpy | DSC, 10° C./min | Onset: 179.3° C., 114 J/g-shown in FIG. 2 |
| Thermogravimetry | TGA, 10° C./min | 0.8 @ 150° C. as seen in FIG. 3 |
| Stoichiometry | $^1$H-NMR (DMSO-d6) | No detectable residual solvent as seen in FIG. 4 |

Bulk Stability

Bulk stability of Form C was evaluated at 25° C./92% RH in an open container, at 40° C./75% RH in an open container and at 60° C. in a tight container over 1 week. Form C is physically and chemically stable after stressed under these conditions as shown in Table 5.

TABLE 5

Bulk stability

| Exp. ID | Initial purity | 99.2% Purity | Color |
|---|---|---|---|
| BS1 | Solid state, 25° C./92% RH, open container, 1 week | | |
|  | Bulk (HPLC) | 99.2% | No color change |
|  | Bulk (XRPD) | Form C | |
| BS2 | Solid state, 40° C./75% RH, open container, 1 week | | |
|  | Bulk (HPLC) | 99.1% | No color change |
|  | Bulk (XRPD) | Form C | |
| BS3 | Solid state, 60° C., tight container, 1 week | | |
|  | Bulk (HPLC) | 99.2% | No color change |
|  | Bulk (XRPD) | Form C | |

The stability of Form C was further investigated under the following conditions with the results summarized in Tables 5A-5F.

TABLE 5A

Condition/Placement Status: 25° C. ± 2° C./60% RH ± 5% RH, Normal

|  |  | Initial | 01 Month | 03 Month | 06 Month |
|---|---|---|---|---|---|
| Appearance | Appearance | Off-white powder | Off-white powder | Off-white powder | Off-white powder |
| Purity (area %), HPLC | Purity (area %), HPLC | 99.2 | 99.3 | 99.2 | 99.3 |
| Impurities (area %), HPLC | SM1 (area %) | <0.05 | <0.05 | <0.05 | <0.05 |
|  | SM2 (area %) | <0.05 | <0.05 | <0.05 | <0.05 |
|  | RRT 1.07 (area %) | 0.77 | 0.71 | 0.77 | 0.73 |

TABLE 5B

Condition/Placement Status: 25° C. ± 2° C./60% RH ± 5% RH, Normal

|  |  | Initial | 01 Month | 03 Month | 06 Month |
|---|---|---|---|---|---|
| Impurities (area %), HPLC | A (area %) | <0.05 | <0.05 | <0.05 | <0.05 |
|  | B (area %) | <0.05 | <0.05 | <0.05 | <0.05 |
|  | C (area %) | <0.05 | <0.05 | <0.05 | <0.05 |
|  | D (area %) | <0.05 | <0.05 | <0.05 | <0.05 |
|  | Unidentified impurity | <0.05 | <0.05 | <0.05 | <0.05 |
| XRPD | XRPD | Conforms with Form C | N/A | N/A | N/A |
| Water content (wt %) | Water content (wt %) | <0.05 | <0.05 | <0.05 | <0.05 |

TABLE 5C

Condition/Placement Status: 25° C. ± 2° C./60% RH ± 5% RH, Normal

|  |  | 09 Month | 12 Month |
|---|---|---|---|
| Appearance | Appearance | Off-white powder | Off-white powder |
| Purity (area %), HPLC | Purity (area %), HPLC | 99.3 | 99.3 |
| Impurities (area %), HPLC | SM1 (area %) | <0.05 | <0.05 |
|  | SM2 (area %) | <0.05 | <0.05 |
|  | RRT 1.07 (area %) | 0.72 | 0.74 |
|  | A (area %) | <0.05 | <0.05 |
|  | B (area %) | <0.05 | <0.05 |

TABLE 5D

| Condition/Placement Status: 25° C. ± 2° C./60% RH ± 5% RH, Normal | | | |
|---|---|---|---|
| | | 09 Month | 12 Month |
| Impurities (area %), HPLC | C (area %) | <0.05 | <0.05 |
| | D (area %) | <0.05 | <0.05 |
| | Unidentified impurity | <0.05 | <0.05 |
| XRPD | XRPD | N/A | Conforms with Form C |
| Water content (wt %) | Water content (wt %) | <0.05 | <0.05 |
| Assay (wt %), HPLC | Assay (wt %), HPLC | 99.4 | 99.4 |

TABLE 5E

| Condition/Placement Status: 40° C. ± 2° C./75% RH ± 5% RH, Normal | | | | | |
|---|---|---|---|---|---|
| | | Initial | 01 Month | 03 Month | 06 Month |
| Appearance | Appearance | Off-white powder | Off-white powder | Off-white powder | Off-white powder |
| Purity (area %), HPLC | Purity (area %), HPLC | 99.2 | 99.3 | 99.2 | 99.3 |
| Impurities (area %), HPLC | SM1 (area %) | <0.05 | <0.05 | <0.05 | <0.05 |
| | SM2 (area %) | <0.05 | <0.05 | <0.05 | <0.05 |
| | RRT 1.07 (area %) | 0.77 | 0.70 | 0.77 | 0.73 |
| | A (area %) | <0.05 | <0.05 | <0.05 | <0.05 |
| | B (area %) | <0.05 | <0.05 | <0.05 | <0.05 |

TABLE 5F

| Condition/Placement Status: 40° C. ± 2° C./75% RH ± 5% RH, Normal | | | | | |
|---|---|---|---|---|---|
| | | Initial | 01 Month | 03 Month | 06 Month |
| Impurities (area %), HPLC | C (area %) | <0.05 | <0.05 | <0.05 | <0.05 |
| | D (area %) | <0.05 | <0.05 | <0.05 | <0.05 |
| | Unidentified impurity | <0.05 | <0.05 | <0.05 | <0.05 |
| XRPD | XRPD | Conforms with Form C | N/A | N/A | Conforms with Form C |
| Water content (wt %) | Water content (wt %) | <0.05 | <0.05 | <0.05 | <0.05 |
| Assay (wt %), HPLC | Assay (wt %), HPLC | 99.4 | 99.7 | 98.7 | 99.1 |

As can be seen above, Form C is stable in conditions where the temperature and relative humidity are altered.

Solubility

The anhydrate Form C (equivalent to 8 mg of free form) was weighed into a 20 mL glass vial. 4 mL of solubility medium was added. Obtained suspensions were stirred at 37° C. at 400 rpm. Some of the suspensions were taken out at 2 hours and 24 hours, respectively. Then they were centrifuged at 3700 at 14,000 rpm for 5 (m. Supernatants were analyzed by HPLC and pH meter for solubility and pH, respectively. Residual solids (wet cakes) were characterized by XRPD to determine physical form.

TABLE 6

| Solubility | | | | |
|---|---|---|---|---|
| Method Solubility at 37 ° C., target concentration 2 mg/ml (in free form), equilibration for 24 hours, LOQ: 0.35 ug/mL | | | | |
| | | | 24 h | |
| Exp. ID | Solubility media | 2 h Solubility (ug/mL) | Solubility (ug/mL) (pH) | XRPD of residual solids |
| ES1 | pH 1.0 HCl solution (0.1N) | 17.01 | 14.58 (1.0) | Form C |
| ES2 | pH 3.0 citrate buffer (50 mM) | 5.97 | 4.08 (3.1) | Form C |
| ES3 | pH 5.0 acetate buffer (50 mM) | 5.44 | 3.85 (5.1) | Form C |
| ES4 | pH 7.0 phosphate buffer (50 mM) | 5.43 | 11.57 (7.3) | Form C |

The results of additional solubility studies are shown in Table 7.

TABLE 7

| | 50° C. | | 25° C. | |
|---|---|---|---|---|
| Solvents | Solubility (mg/mL solvent) | XRPD | Solubility (mg/mL solvent) | XRPD |
| Water | ~0 | Form C | ~1 | Form C |
| Ethanol | 64 | | 27 | |
| Acetone | 122 | | 66 | |
| THF | >200 | n/a | 247 | |
| EA | 58 | Form C | 32 | |
| Heptane | ~3 | | ~2 | |
| 2-MeTHF | 154 | | 117 | |
| Toluene | 5 | | 5 | |
| MEK | 110 | | 63 | |
| IPA | 29 | | 14 | |
| n-PrOH | 48 | | 21 | |
| MCH | ~3 | | ~3 | |
| MIBK | 28 | | 21 | |

These data indicate that Form C has high solubility in acetone, THF, 2-MeTHF, and MEK, while having poor solubility in water, n-heptane, and MCH. As there may be potential Form A/H (Anhydrate) or Form I (THF solvate) in water or THF system according to the polymorph screening report, the use of water and THF were avoided in following study. To achieve high yield for the crystallization process, the additional solubility was measured in acetone, 2-MeTHF and MEK in combination of anti-solvent n-hep and MCH at 25° C., as shown in Table 8.

TABLE 8

| Solubility of in mixture solvents | | |
|---|---|---|
| | 25 (° C.) | |
| Solvent Systems (v/v) | Solubility (mg/mL) | XRPD |
| Acetone/MCH = 1/1 | 30 | Form C |
| Acetone/MCH = 1/2 | 15 | |
| MEK/MCH = 1/1 | 20 | |
| MEK/MCH = 1/2 | 9 | |
| 2-MeTHF/MCH = 1/1 | 18 | |
| 2-MeTHF/MCH = 1/2 | 6 | |
| 2-MeTHF/MCH = 1/3 | ~4 | |

TABLE 8-continued

Solubility of in mixture solvents

| Solvent Systems (v/v) | 25 (° C.) Solubility (mg/mL) | XRPD |
|---|---|---|
| Acetone/n-hep = 1/1 | 18 | |
| Acetone/n-hep = 1/2 | 10 | |
| Acetone/n-hep = 1/3 | 5 | |
| MEK/n-hep = 1/1 | 16 | |
| MEK/n-hep = 1/2 | 6 | |
| MEK/n-hep = 1/3 | ~3 | |
| 2-ME-THF/n-hep = 1/1 | 13 | |
| 2-ME-THF/n-hep = 1/2 | ~4 | |
| 2-ME-THF/n-hep = 1/3 | ~2 | |

These data indicate that solubility decreased as more anti-solvent was added to MEK, 2-MeTHF and acetone solvents.

Additional solubility studies were performed in 2-MeTHF in combination of anti-solvent n-hep at 50° C., as shown in Table 9.

| Solvent Systems (v/v) | 50 (° C.) Solubility (mg/mL) | XRPD |
|---|---|---|
| 2-ME-THF/n-hep = 4/0.5 | 122 | Form C |
| 2-ME-THF/n-hep = 4/1 | 90 | |
| 2-ME-THF/n-hep = 4/2 | 49 | |
| 2-ME-THF/n-hep = 4/4 | 21 | |
| 2-ME-THF/n-hep = 4/8 | 10 | |
| 2-ME-THF/n-hep = 4/12 | 5 | |

The solution state chemical stability was carried out in acetone, MEK, and 2-MeTHF solvent systems at 50° C. and 55° C. The results are summarized in Table 10. The data indicate that the compound was stable after 48 h holding in both acetone and 2-MeTHF systems. The purity of the compound degraded from 99.43% to 98.27% after 48 h holding at 55° C. in MEK solvent system.

TABLE 10

Solution state chemical stability study of at 50° C. and 55° C.

| Solvent system | Concentration (mg/mL of solvent) | T/° C. | Purity (a %) 0 h | 6 h | 24 h | 48 h |
|---|---|---|---|---|---|---|
| Acetone | ~10 mg/ml | 50 | 99.54% | 99.50% | 99.51% | 99.69% |
| MEK | | 55 | 99.43% | 99.23% | 98.54% | 98.27% |
| 2-MeTHF | | 55 | 99.35% | 99.55% | 99.62% | 99.62% |

2-MeTHF/n-hep was selected as the potential solvent system for the crystallization. The solution state chemical stability was carried out in 2-MeTHF solvent systems at higher temperature (60° C. and 70° C.). The data indicate that the compound was stable after 48 h holding in 2-MeTHF at 60° C. and 70° C. The solution state chemical stability was carried out in 2-MeTHF/n-hep=1v/1v solvent system at 70° C. and the data indicate that the compound was stable after 48 h holding in the system at 70° C.

TABLE 11

Solution state chemical stability study of at 60° C. and 70° C.

| Solvent system | Concentration (mg/ml of solvent) | T/° C. | Purity (a %) 0 h | 24 h | 48 h |
|---|---|---|---|---|---|
| 2-MeTHF | ~10 mg/ml | 60 | 99.54% | 99.69% | 99.56% |
| | | 70 | 99.53% | 99.70% | 99.44% |
| 2-MeTHF/ n-hep = 1 v/1 v | | 70 | 98.45% | 98.44% | 98.44% |

Anti-Solvent Crystallization

According to the solubility and chemical stability data, anti-solvent crystallization experiments systems were carried out in in acetone/n-hep and 2-MeTHF/n-hep systems as shown below.

Preliminary anti-solvent crystallization in 2-MeTHF/n-hep:
1. Dissolve in 8v 2-MeTHF at 50° C.
2. Adjust to 25° C. in 0.5 h
3. Seed (10 mg)
4. Stir for 1 h at 25° C.
5. Charge 24v n-hep in 4 h at 25° C.
6. Take sample for XRPD-1 and PLM-1 analysis.
7. Stir for 15 h at 25° C.
8. Take sample for XRPD-2, PLM-2 and assay-1 analysis.
9. Stir for 8 h at 25° C.
10. Filter and wash the cake with 2v 2-MeTHF/n-hep=1v/3v.
11. Dry the wet cake under vacuum at 50° C.
12. Obtain material After adding n-hep, XRPD showed Form C even after holding at 25° C. (about 6% mother liquor (ML) loss). The dried product showed 99.41% purity with residual 2-MeTHF of 0.46% and 0.07% residual n-hep.

Preliminary anti-solvent crystallization in acetone/n-hep:
1. Dissolve in 9v Acetone at 50° C.
2. Adjust to 45° C.
3. Seed (10 mg)
4. Stir for 0.5 h at 45° C. (thin suspension)
5. Adjust to 42° C.
6. Stir for 1 h at 42° C. (suspension with more solids)
7. Adjust to 25° C. in about 3.5 h.
8. Take sample for XRPD-1 and PLM-1 analysis.
9. Charge 27v n-hep in 4.5 h at 25° C.
10. Stir for 12 h at 25° C.
11. Take sample for XRPD-2, PLM-2 and assay-1 analysis.
12. Stir for 6 h at 25° C.
13. Adjust to 5° C. in 4 h.
14. Stir for 14 h at 5° C.
15. Take sample for XRPD-3, PLM-3 and assay-2 analysis.
16. Filter and wash the cake with 2v acetone/n-hep=1v/3v.
17. Dry the wet cake under vacuum at 50° C.
18. Obtain material.

Before adding n-hep, XRPD indicated Form C. After adding n-hep, the XRPD reflected Form C even after holding at 25° C. (about 17% ML loss). Before filtration, ML loss was about 12%. The dried product had 99.61% purity with 0.03% residual acetone and 0.04% residual n-hep.

Process Optimization in 2-MeTHF/n-heptane

According to the results of the preliminary anti-solvent crystallization in 2-MeTHF/n-hep and acetone/n-hep, 2-MeTHF/n-hep system was decided as the leading crystallization system. Two use test experiments were carried out to achieve 11 g of crystallized product.

The results can be seen in Table 12.

TABLE 12

| | | | Results | | | |
|---|---|---|---|---|---|---|
| | After adding anti-solvent | Before filtration | dry product | | | |
| Temp. | XRPD | XRPD | XRPD | Purity | Residual solvent | Yield |
| 25° C. | Form C | Form C | Form C | 99.46% | 2-MeTHF: 0.28% n-hep: 0.06% | ML loss: ~5% (Assay: 0.21%) |
| 50° C. 2-MeTHF/n-hep = 4 v/1 v | Form C | Form C | Form C | 99.49% | 2-MeTHF: 0.07% n-hep: 0.05% | ML loss: ~4% (Assay: 0.17%) |

With the results of experiment above, the 11 g scale-up experiment was carried out using the following procedures.
1. Dissolve in 8 v 2-MeTHF at 50° C.
2. Charge 1.5v n-hep in 1 h at 50° C.
3. Seed (110 mg)
4. Stir for 1.5 h at 50° C.
5. Charge 22.2v n-hep in 7 h at 50° C.
6. Take sample for XRPD-1.
7. Stir for 15 h at 50° C.
8. Take sample for XRPD-2.
9. Stir for 20 h at 50° C.
10. Take sample for XRPD-3.
11. Charge 0.3v n-hep in 1 h at 50° C.
12. Stir for 1 h at 50° C.
13. Adjust to 25° C. in 5 h
14. Stir for 17 h at 25° C.
15. Take sample for XRPD-4, Purity and assay-1 analysis.
16. Filter and wash the cake with 2v 2-MeTHF/n-hep=1v/3v.
17. Dry the wet cake under vacuum at 50° C.
18. Obtain material After adding n-hep, XRPD shows Form C with an extra peak. After holding at 50° C. for 15 h and 35 h, XRPD showed again Form C with an extra peak (ML loss of about 4%). Because an extra peak was observed in XRPD, the process was further optimized using the procedure below.
1. Dissolve in 8v 2-MeTHF at 50° C.
2. Charge 2v n-hep in 1-3 h at 50° C.
3. Seed (150 mg)
4. Stir for 1-18 h at 50° C. (thin suspension)
5. Charge 2v n-hep in 2-3 h at 50° C.
6. Take sample for XRPD analysis.
7. Stir for 2-4 h at 50° C.
8. Take sample for XRPD analysis.
9. Charge 20v n-hep in 6-8 h at 50° C.
10. Stir for 2 h at 50° C.
11. Adjust to 25° C. in 5 h
12. Stir for 2 h at 25° C.
13. Take sample for XRPD analysis.
14. Stir at 25° C. for 6-15 h
15. Filter and wash the cake with 2v 2-MeTHF/n-hep=1v/3v.
16. Dry the wet cake under vacuum at 50° C.
17. Obtained the material This procedure was performed twice with XRPD showing Form C both times. Purity was measured at 99.24% and 97.86%.

Hygroscopicity

Hygroscopicity of Form C was evaluated by dynamic vapor sorption (DVS) test at 25° C. Form C is non-hygroscopic below 90% relative humidity (RH). Form C absorbs about 0.2% water in 95% RH at 25° C. After the DVS test, the obtained sample was still in Form C.

Evaluation of Form C

Form C is the optimal polymorph identified. Its stability, solubility, hygroscopicity and feasibility of formulation process were evaluated as described above.

Various modifications of the disclosure, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

The invention claimed is:

1. A crystalline form of 3-(5-(2-hydroxy-2-methylpropoxy)-6-methylpyrazin-2-yl)-1H-indole-7-carbonitrile.

2. The crystalline form of claim 1, wherein the crystalline form is anhydrous.

3. The crystalline form of claim 1, wherein the crystalline form is characterized by an XRPD diffractogram having peaks expressed in degrees-2-theta at angles (+0.2 degrees) of 23.8, 20.7, and 11.7.

4. The crystalline form of claim 1, wherein the crystalline form is characterized by an XRPD diffractogram having peaks expressed in degrees-2-theta at angles (+0.2 degrees) of 23.8, 20.7, 11.7, and 24.6.

5. The crystalline form of claim 1, wherein the crystalline form is characterized by an XRPD diffractogram having peaks expressed in degrees-2-theta at angles (+0.2 degrees) of 23.8, 20.7, 11.7, 24.6, and 15.8.

6. The crystalline form of claim 1, wherein the crystalline form has the XRPD diffractogram as depicted in FIG. 1.

7. The crystalline form of claim 1 having a DSC thermogram characterized by an endotherm with an onset temperature of about 179° C.

8. The crystalline form of claim 1 having a DSC thermogram characterized by an endotherm with an onset temperature of 179.3° C.

9. A pharmaceutical composition comprising the crystalline form of claim 1 and a pharmaceutically acceptable carrier.

10. A process for preparing the crystalline form of claim 1 comprising dissolving 3-(5-(2-hydroxy-2-methylpropoxy)-6-methylpyrazin-2-yl)-1H-indole-7-carbonitrile to a first solvent, adding a second solvent to form a slurry, and filtering the slurry to isolate the crystalline form of 3-(5-(2-hydroxy-2-methylpropoxy)-6-methylpyrazin-2-yl)-1H-indole-7-carbonitrile.

11. The process of claim 10, wherein the first solvent is selected from the group consisting of acetone, ethyl acetate, methyl tert-butyl ether (MTBE), and 2-methyltetrahydrofuran (MeTHF), or a combination thereof.

12. The process of claim 11, wherein the second solvent is heptane.

13. The process of claim 10, wherein the first solvent is 2-methyltetrahydrofuran (MeTHF).

* * * * *